(12) United States Patent
Iwasaki et al.

(10) Patent No.: US 9,848,124 B2
(45) Date of Patent: Dec. 19, 2017

(54) ENDOSCOPE SYSTEM AND ENDOSCOPE VIDEO PROCESSOR

(71) Applicant: OLYMPUS CORPORATION, Tokyo (JP)

(72) Inventors: Tomoki Iwasaki, Fuchu (JP); Takeo Suzuki, Hachioji (JP); Kazuki Honda, Higashiyamato (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/297,186

(22) Filed: Oct. 19, 2016

(65) Prior Publication Data

US 2017/0041537 A1 Feb. 9, 2017

Related U.S. Application Data

(63) Continuation of application No. PCT/JP2015/085510, filed on Dec. 18, 2015.

(30) Foreign Application Priority Data

Dec. 22, 2014 (JP) ................. 2014-258920

(51) Int. Cl.
| | |
|---|---|
| *H04N 5/232* | (2006.01) |
| *A61B 1/04* | (2006.01) |
| *G02B 23/24* | (2006.01) |
| *G02B 23/26* | (2006.01) |
| *A61B 1/00* | (2006.01) |
| *H04N 5/225* | (2006.01) |

(52) U.S. Cl.
CPC ..... *H04N 5/23238* (2013.01); *A61B 1/00009* (2013.01); *A61B 1/04* (2013.01);
(Continued)

(58) Field of Classification Search
CPC ...... A61B 1/04; A61B 1/00009; G02B 23/24; G02B 23/26; H04N 2005/2255;
(Continued)

(56) References Cited

U.S. PATENT DOCUMENTS

2013/0076879 A1* 3/2013 On .................... A61B 1/00009
348/65
2013/0109917 A1* 5/2013 Kase .................. A61B 1/0615
600/109
(Continued)

FOREIGN PATENT DOCUMENTS

| CN | 103841879 A | 6/2014 |
|---|---|---|
| EP | 2929830 A1 | 10/2015 |

(Continued)

OTHER PUBLICATIONS

International Search Report dated Mar. 8, 2016 issued in PCT/JP2015/085510.

*Primary Examiner* — Zhihan Zhou
(74) *Attorney, Agent, or Firm* — Scully, Scott, Murphy & Presser, P.C.

(57) ABSTRACT

An endoscope system has an insertion portion, a forward observation window configured to acquire a forward-field-of-view image, a lateral observation window configured to acquire a lateral-field-of-view image, an image pickup device and a video processor. A positional displacement correcting portion of the video processor detects a positional relationship between a portion where the forward-field-of-view image is formed and a portion where the lateral-field-of-view image is formed, on the image pickup device, and generates displacement amount data. A boundary correcting portion generates an image signal in which the forward-field-of-view image and the lateral-field-of-view image are arranged with an image center point provided in the portion and an image center point provided in the portion caused to correspond to each other, based on the displacement amount data.

10 Claims, 12 Drawing Sheets

(52) U.S. Cl.
CPC ............. *G02B 23/24* (2013.01); *G02B 23/26* (2013.01); *H04N 5/2256* (2013.01); *H04N 5/2258* (2013.01); *H04N 5/23293* (2013.01); *H04N 2005/2255* (2013.01)

(58) Field of Classification Search
CPC ............. H04N 5/2258; H04N 5/23238; H04N 5/23293; H04N 5/2256
USPC .......................................................... 348/65
See application file for complete search history.

(56) References Cited

U.S. PATENT DOCUMENTS

| | | | | |
|---|---|---|---|---|
| 2014/0081083 A1* | 3/2014 | Morita | ................ | A61B 1/0646 600/109 |
| 2014/0142381 A1* | 5/2014 | Bae | ................... | A61B 1/00177 600/109 |
| 2014/0204187 A1* | 7/2014 | Sasaki | ............... | A61B 1/00009 348/65 |
| 2014/0307072 A1* | 10/2014 | Takahashi | .......... | H04N 5/23296 348/65 |
| 2015/0265136 A1 | 9/2015 | Honda | | |

FOREIGN PATENT DOCUMENTS

| | | | | |
|---|---|---|---|---|
| JP | 2010-099178 A | 5/2010 | | |
| JP | 2012-157577 A | 8/2012 | | |
| JP | 2013-066648 A | 4/2013 | | |
| JP | WO 2013047215 A1 * | 4/2013 | ......... | A61B 1/00009 |
| JP | 2015-119827 A | 7/2015 | | |
| WO | WO 2014/088076 A1 | 6/2014 | | |

* cited by examiner

US 9,848,124 B2

ENDOSCOPE SYSTEM AND ENDOSCOPE VIDEO PROCESSOR

CROSS REFERENCE TO RELATED APPLICATION

This application is a continuation application of PCT/JP2015/085510 filed on Dec. 18, 2015 and claims benefit of Japanese Application No. 2014-258920 filed in Japan on Dec. 22, 2014, the entire contents of which are incorporated herein by this reference.

BACKGROUND OF THE INVENTION

1. Field of the Invention

The present invention relates to an endoscope system and an endoscope video processor, and more particularly to an endoscope system capable of observing a forward field of view and a lateral field of view independently and simultaneously, and an endoscope video processor.

2. Description of the Related Art

Endoscope systems provided with an endoscope for picking up an image of an object inside a subject, an image processing apparatus for generating an observed image of the object picked up by the endoscope, and the like are widely known in a medical field, an industrial field and the like.

Further, some endoscope systems are capable of observing a subject with a wide field of view in order to prevent a lesion portion from being overlooked. For example, Japanese Patent Application Laid-Open Publication No. 2013-66648 discloses an endoscope capable of simultaneously acquiring a forward-field-of-view image and a lateral-field-of-view image and displaying the forward-field-of-view image and the lateral-field-of-view image on a display portion.

SUMMARY OF THE INVENTION

An endoscope system of an aspect of the present invention includes: an insertion portion configured to be inserted into an inside of an object; a first object image acquiring portion provided on the insertion portion and configured to acquire a first object image from a first area of the object; a second object image acquiring portion provided on the insertion portion and configured to acquire a second object image from a second area of the object different from the first area; an image pickup portion configured to pick up the first object image and the second object image; an object image position detecting portion configured to detect a positional relationship between a first image forming area where the first object image is formed and a second image forming area where the second object image is formed, on the image pickup portion and generate positional relationship detection information; and an image signal generating portion configured to generate an image signal in which the first object image and the second object image are arranged with a first reference position provided in the first image forming area and a second reference position provided in the second image forming area caused to correspond to each other based on the positional relationship detection information.

An endoscope video processor of the present invention is an endoscope video processor into which a first object image acquired by an image pickup portion of an endoscope inserted inside an object and a second object image acquired from a direction different from a direction for the first object image are inputted, the endoscope video processor including: an object image position detecting portion configured to detect a positional relationship between a first image forming area where the first object image is formed on the image pickup portion and a second image forming area where the second object image is formed on the image pickup portion and generate positional relationship detection information; and an image signal generating portion configured to generate an image signal in which the first object image and the second object image are arranged with a first reference position provided in the first image forming area and a second reference position provided in the second image forming area caused to correspond to each other based on the positional relationship detection information.

DETAILED DESCRIPTION OF THE PREFERRED EMBODIMENT(S)

Embodiments of the present invention will be described below with reference to drawings.

First Embodiment (System Configuration)

Figure 1:
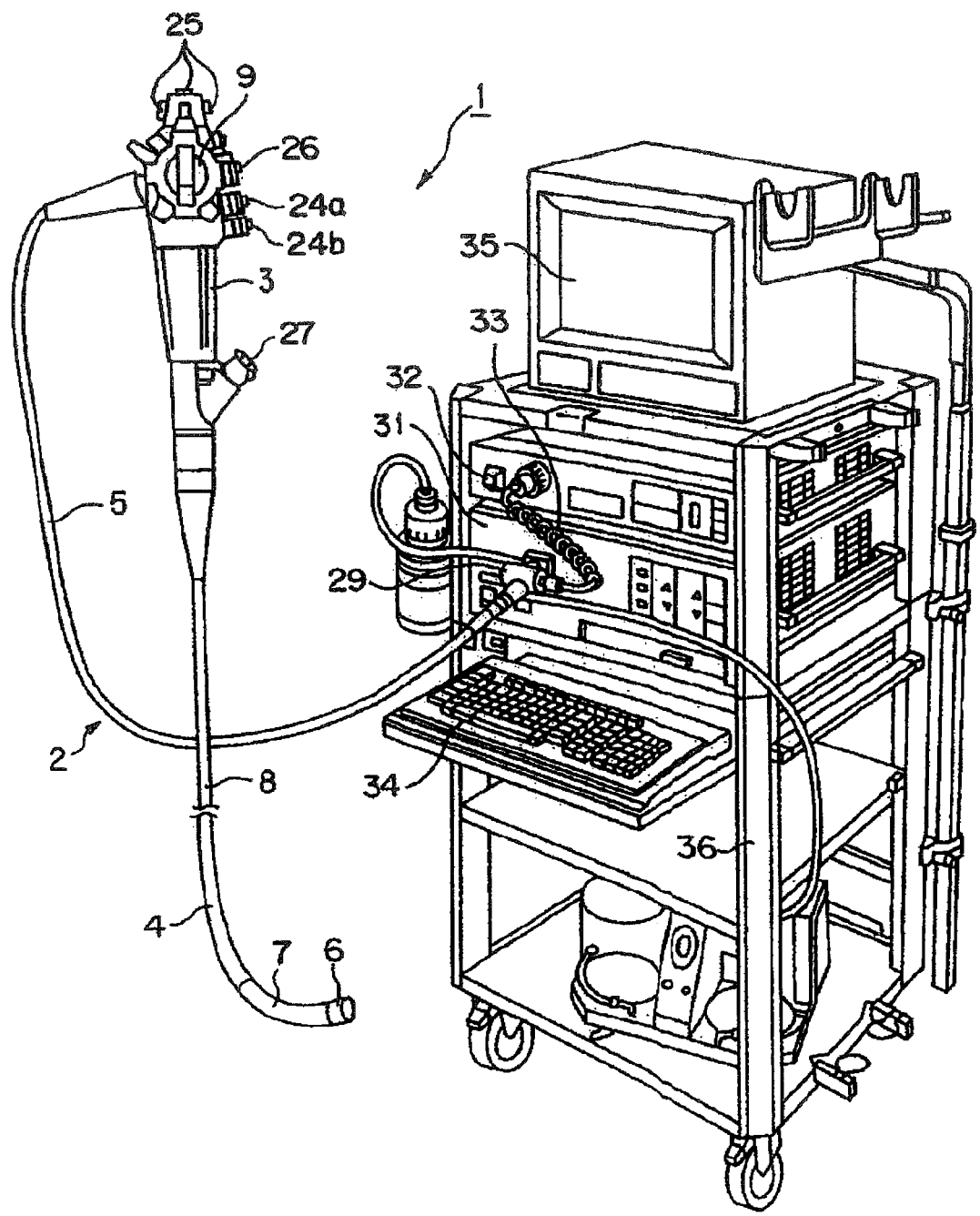
FIG. 1 is a diagram showing a configuration of an endoscope system according to a first embodiment of the present invention.
Figure 2:
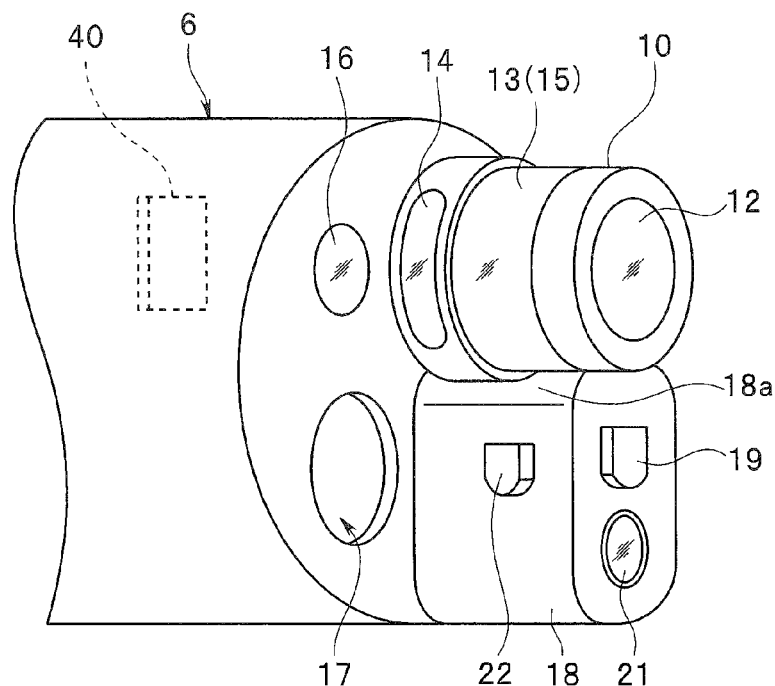
FIG. 2 is a perspective view showing a configuration of a distal end portion of an insertion portion of an endoscope according to the first embodiment of the present invention.
Figure 3:
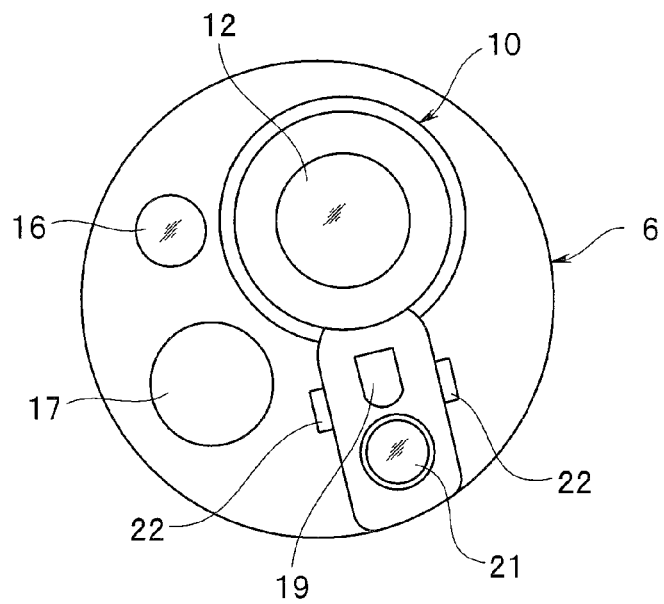
FIG. 3 is a front view showing the configuration of the distal end portion of the insertion portion of the endoscope according to the first embodiment of the present invention.
Figure 4:
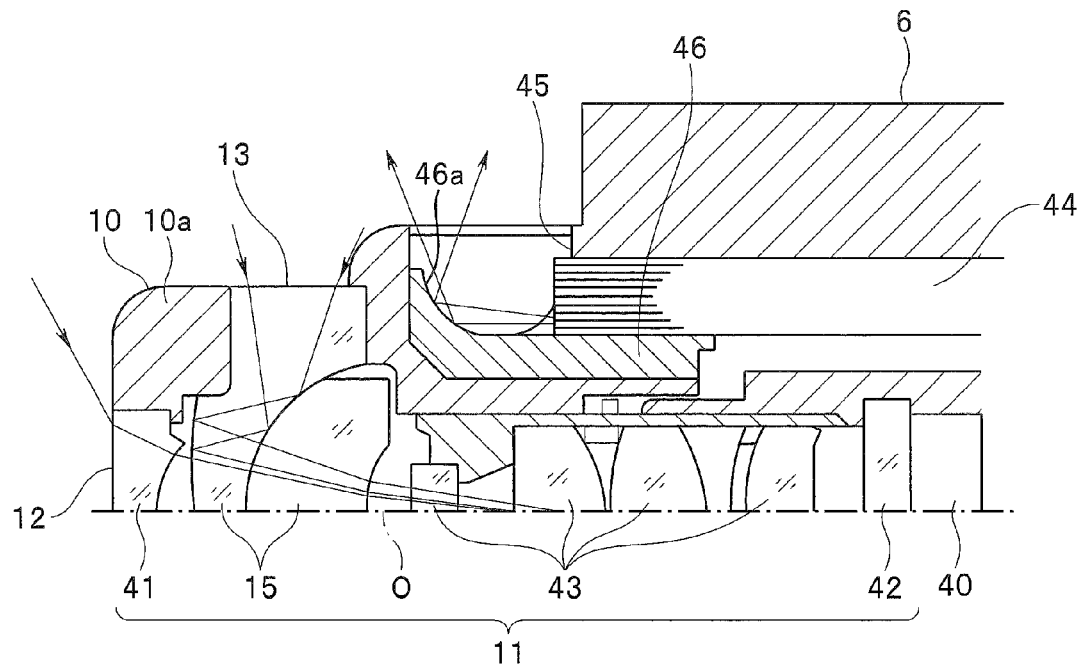
FIG. 4 is a sectional view of main portions showing the configuration of the distal end portion of the insertion portion in the endoscope system of the first embodiment of the present invention.
Figure 5:
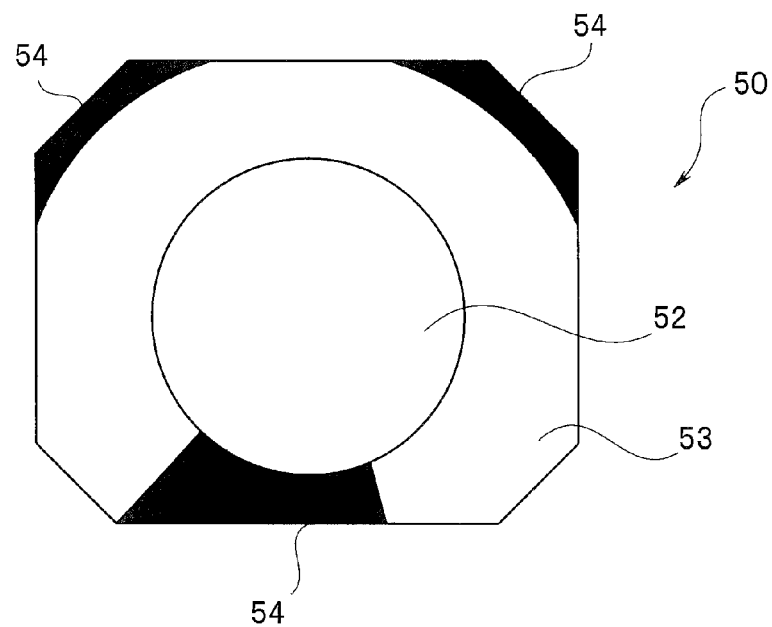
FIG. 5 is a diagram showing an example of an observed image displayed on a monitor by image processing by a video processor of the endoscope system according to the first embodiment of the present invention.

First, description will be made on a configuration of an endoscope system of a first embodiment with use of FIGS. 1 to 4. FIG. 1 is a diagram showing a configuration of an endoscope system according to the first embodiment. FIG. 2 is a perspective view showing a configuration of a distal end portion of an insertion portion of an endoscope. FIG. 3 is a front view showing the configuration of the distal end portion of the insertion portion of the endoscope. FIG. 4 is a sectional view of main portions showing the configuration of the distal end portion of the insertion portion in the endoscope system of the first embodiment. FIG. 5 is a diagram showing an example of an observed image displayed on a monitor by image processing by a video processor of the endoscope system.

As shown in FIG. 1, an endoscope system 1 has an endoscope 2 configured to pick up an image of an observation target substance (an object) and output an image pickup signal, a light source apparatus 31 configured to supply illuminating light for illuminating the observation target substance, a video processor 32 which is an image processing apparatus configured to generate and output a video signal corresponding to the image pickup signal, and a monitor 35 configured to display an observed image which is an endoscopic image corresponding to the video signal.

The endoscope 2 is configured having an operation portion 3 configured to be grasped by a surgeon to perform an operation, an elongated insertion portion 4 formed on a distal end side of the operation portion 3 and configured to be inserted into a body cavity or the like, which is an object, and a universal cord 5 one end portion of which is provided so as to extend from a side portion of the operation portion 3.

The endoscope 2 of the present embodiment is a wide-angle endoscope making it possible to observe a field of view of 180 degrees or more by causing a plurality of field-of-view images to be displayed. It is realized to prevent a lesion at such a place that it is difficult to see the lesion only by front observation, such as a back of folds and a boundary of organs, from being overlooked in a body cavity, especially in a large intestine. At time of inserting the insertion portion 4 of the endoscope 2 into a large intestine, actions such as a twist, a reciprocating motion and a temporary fixation by hooking an intestinal wall occur on the insertion portion 4, similarly to an ordinary large intestine endoscope.

The insertion portion 4 to be inserted into an inside of an object is configured having a rigid distal end portion 6 provided on a most distal end side, a bendable bending portion 7 provided at a rear end of the distal end portion 6, and a long flexible tube portion 8 having flexibility provided on a rear end of the bending portion 7. Further, the bending portion 7 performs a bending action corresponding to an operation of a bending operation lever 9 provided on the operation portion 3.

On the other hand, as shown in FIG. 2, a cylindrical portion 10 in a cylindrical shape provided projecting from a position eccentrically displaced upward from a center of a distal end face of the distal end portion 6 is formed on the distal end portion 6 of the insertion portion 4.

On a distal end portion of the cylindrical portion 10, an objective optical system not shown is provided which is for observation of both of a forward field of view and a lateral field of view. Further, the distal end portion of the cylindrical portion 10 is configured having a forward observation window 12 arranged at a position corresponding to a forward direction of the objective optical system not shown, and a lateral observation window 13 arranged at a position corresponding to a lateral-viewing direction of the objective optical system not shown. Furthermore, lateral illuminating windows 14 configured to emit light for illuminating a lateral direction are formed in a vicinity of a proximal end of the cylindrical portion 10. The lateral observation window 13 is arranged on a more proximal end side of the insertion portion 4 than the forward observation window 12.

The lateral observation window 13 is provided with a lateral-viewing mirror lens 15 for making it possible to acquire a lateral-field-of-view image by capturing return light, that is, reflected light from an observation target substance which is caused to be incident from around the cylindrical portion 10 in a cylindrical shape within a lateral field of view.

Note that, at an image forming position of the objective optical system not shown, an image pickup surface of an image pickup device 40 is arranged so that an image of an observation target substance within a field of view of the forward observation window 12 is formed at a central part as a circular-shaped forward-field-of-view image, and an image of the observation target substance within a field of view of the lateral observation window 13 is formed on an outer circumferential portion of the forward-field-of-view image as a ring-shaped lateral-field-of-view image.

That is, the forward observation window 12 is provided on the insertion portion 4 and constitutes a first object image acquiring portion configured to acquire a first object image from a first area including a forward direction, which is a first direction, and the lateral observation window 13 is provided on the insertion portion 4 and constitutes a second object image acquiring portion configured to acquire a second object image from a second area including a lateral direction, which is a second direction different from the forward direction. In other words, the forward observation window 12 is a forward image acquiring portion configured to acquire an object image in an area including the forward direction of the insertion portion, and the lateral observation window 13 is a lateral image acquiring portion configured to acquire an object image in an area including the lateral direction of the insertion portion.

The forward observation window 12 is arranged on the distal end portion 6 in a longitudinal direction of the insertion portion 4 so as to acquire an object image from the forward direction, which is a direction in which the insertion portion 4 is inserted, and the lateral observation window 13 is arranged along an outer diameter direction of the insertion portion 4 so as to acquire an object image from the lateral direction. In other words, the first object image is an object image in the first direction including the forward direction of the insertion portion substantially parallel to the longitudinal direction of the insertion portion 4, and the second object image is an object image in the second direction including the lateral direction of the insertion portion crossing the longitudinal direction of the insertion portion 4, for example, at a right angle.

Then, the image pickup device 40, which is an image pickup portion, photoelectrically converts the forward-field-of-view image and the lateral-field-of-view image on one image pickup surface, and an image signal of the forward-field-of-view image and an image signal of the lateral-field-of-view image are generated by being cut out from the images obtained by the image pickup device 40. That is, the image pickup device 40 constitutes an image pickup portion configured to pick up the first object image and the second object image, and the image pickup device 40 is electrically connected to the video processor 32.

On the distal end face of the distal end portion 6, a forward illuminating window 16 arranged at a position adjoining the cylindrical portion 10 and configured to emit illuminating light within a range of the forward field of view of the forward observation window 12, and a distal end opening 17 communicating to a treatment instrument channel not shown, which is arranged in the insertion portion 4 and formed by a tube or the like, and capable of causing a distal end portion of a treatment instrument inserted in the treatment instrument channel to project.

Further, the distal end portion 6 of the insertion portion 4 has a support portion 18 provided so as to project from the distal end face of the distal end portion 6, and the support portion 18 is positioned adjoining a lower part side of the cylindrical portion 10.

The support portion 18 is configured being capable of supporting or holding respective projecting members arranged so as to be caused to project from the distal end face of the distal end portion 6. More specifically, the support portion 18 is configured so as to be capable of supporting or holding each of a forward observation window nozzle portion 19 configured to eject gas or liquid for cleaning the forward observation window 12, and lateral observation window nozzle portions 22 configured to eject gas or liquid for cleaning another forward illuminating window 21 configured to emit light for illuminating the forward direction and the lateral observation window 13, as the respective projecting members described above.

On the other hand, the support portion 18 is formed having a blocking portion 18a, which is an optical blocking member for preventing such a lateral-field-of-view image that includes any of the respective projecting members described above, which are substances different from an original observation target substance, from being acquired by the respective projecting members appearing in the lateral field of view. That is, by providing the blocking portion 18a on the support portion 18, it is possible to obtain such a lateral-viewing field-of-view image that includes none of the forward observation window nozzle portion 19, the forward illuminating window 21 and the lateral observation window nozzle portions 22.

As shown in FIGS. 2 and 3, the lateral observation window nozzle portions 22 are provided at two positions of the support portion 18 and arranged so that distal ends project from a side face of the support portion 18.

As shown in FIG. 1, the operation portion 3 is provided with a air/liquid feeding operation button 24a capable of giving an operation instruction to cause gas or liquid for cleaning the forward observation window 12 to be ejected from the forward observation window nozzle portion 19, and a air/liquid feeding operation button 24b capable of giving an operation instruction to cause gas or liquid for cleaning the lateral observation window 13 to be ejected from the lateral observation window nozzle portions 22. It is possible to switch between air feeding and liquid feeding by pressing down the air/liquid feeding operation buttons 24a and 24b. Further, though the plurality of air/liquid feeding operation buttons are provided to correspond to the respective nozzle portions in the present embodiment, it is also possible, for example, to cause gas or liquid to be ejected from both of the forward observation window nozzle portion 19 and the lateral observation window nozzle portions 22 by an operation of one air/liquid feeding operation button.

A plurality of scope switches 25 are provided on a top portion of the operation portion 3 and have a configuration in which functions for the respective switches can be allocated so as to cause described various signals corresponding to on or off, which are usable in the endoscope 2, to be outputted. More specifically, start and stop of forward water feeding, execution and release of freeze for photographing a still image, and a function of causing a signal corresponding to a notification of a use state of a treatment instrument and the like to be outputted can be allocated as functions of the respective switches.

Note that, in the present embodiment, a function of at least one of the air/liquid feeding operation buttons 24a and 24b may be allocated to any one of the scope switches 25.

Further, on the operation portion 3, a suction operation button 26 capable of giving an instruction to suck and collect mucus and the like in a body cavity from the distal end opening 17 to a suction unit or the like not shown is arranged.

The mucus and the like in the body cavity sucked in response to an action of the suction unit or the like not shown is collected into a suction bottle or the like of the suction unit not shown via the distal end opening 17, the treatment instrument channel not shown in the insertion portion 4, and a treatment instrument insertion port 27 provided near a front end of the operation portion 3.

The treatment instrument insertion port 27 communicates to the treatment instrument channel not shown in the insertion portion 4 and is formed as an opening through which a treatment instrument not shown can be inserted. That is, a surgeon can perform treatment using a treatment instrument by inserting the treatment instrument from the treatment instrument insertion port 27 and causing a distal end side of the treatment instrument to project from the distal end opening 17.

On the other hand, as shown in FIG. 1, the other end portion of the universal cord 5 is provided with a connector 29 connectable to the light source apparatus 31.

A distal end portion of the connector 29 is provided with a pipe sleeve (not shown) to be a liquid conduit connection end portion and a light guide pipe sleeve (not shown) to be an illuminating light supply end portion. Further, an electrical contact portion (not shown) to which one end portion of a connection cable 33 can be connected is provided on a side face of the connector 29. Furthermore, the other end portion of the connection cable 33 is provided with a connector for electrically connecting the endoscope 2 and the video processor 32.

The universal cord 5 includes a plurality of signal lines for transmitting various electrical signals and a light guide for transmitting illuminating light supplied from the light source apparatus 31 in a bundled state.

The light guide included in the insertion portion 4 to the universal cord 5 has such a configuration that a light-emission-side end portion is branched in at least two directions near the insertion portion 4, and a light emission end face on one side is arranged in the forward illuminating windows 16 and 21, while a light emission end face on the other side is arranged in the lateral illuminating windows 14. Further, the light guide has such a configuration that an end portion on a light incidence side is arranged in the light guide pipe sleeve of the connector 29.

The video processor 32, which is an image processing apparatus and an image signal generation apparatus, outputs a drive signal for driving the image pickup device 40 provided on the distal end portion 6 of the endoscope 2. Then, the video processor 32 performs signal processing (cutting out a predetermined area) for an image pickup signal outputted from the image pickup device 40 based on a use state of the endoscope 2, and, thereby, generate a video signal and output the video signal to the monitor 35.

Peripheral devices such as the light source apparatus 31, the video processor 32 and the monitor 35 are arranged on a stand 36 together with a keyboard 34 for performing input of patient information and the like.

The light source apparatus 31 includes a lamp. Light emitted from the lamp is guided to a connector portion to which the connector 29 of the universal cord 5 is connected, via the light guide. The light source apparatus 31 supplies illuminating light to the light guide in the universal cord 5.

FIG. 4 is a sectional view of main portions showing a configuration of the distal end portion 6 of the insertion portion 4 in the endoscope system of the first embodiment, which shows a configuration of an objective optical system 11 covering the forward direction and the lateral direction, and peripheral portions of the lateral illuminating windows 14.

The objective optical system 11 which forms an image on the image pickup device 40 is formed by arranging a forward lens 41, a mirror lens 15 and a rear lens group 43, each lens being in a rotationally symmetrical shape, on an optical axis corresponding to an image pickup center O along a central axis of the cylindrical portion 10 projecting from the distal end portion 6. Note that cover glass 42 is provided on a front face of the image pickup device 40. The forward lens 41, the mirror lens 15 and the rear lens group 43 are fixed to a lens frame in the cylindrical portion 10.

The forward lens 41 constituting the objective optical system 11 and provided in the circular-shaped forward observation window 12 forms a wide-angle forward field of view, with its distal end side along an insertion direction of the insertion portion 4 as an observation field of view.

The mirror lens 15 as a catoptric system, which is arranged immediately after the forward lens 41, is configured as shown in FIG. 4 by what is obtained by bonding two lenses together which reflect light caused to be incident from a side face direction twice by a bonded surface and a front face to guide the light to the rear lens group 43 side.

Note that a lens part of the mirror lens 15 facing the forward lens 41 also has a function of refracting light from the forward lens 41 and guiding the light to the rear lens group 43 side.

By the mirror lens 15 provided in the lateral observation window 13, the lateral observation window 13 forms a substantially ring-shaped observation field of view covering an entire circumference in a circumferential direction of the insertion portion while having a predetermined view angle, with an optical axis in a lateral direction relative to a long axis direction of the insertion portion as a substantial center.

Note that FIG. 4 shows schematic routes of a light beam incident on the forward lens 41 forming the forward observation window 12 from an object side within its field of view and a light beam incident on the mirror lens 15 forming the lateral observation window 13 from the object side within its field of view.

On the image pickup surface of the image pickup device 40, an image of an object within the forward field of view provided facing the insertion direction by the forward lens 41 of the forward observation window 12 is formed in a circular shape on a center side, and the image is acquired as a forward-field-of-view image. Further, on the image pickup surface, an image of the object within the lateral field of view is formed in a ring shape by the mirror lens 15 facing the lateral observation window 13 on an outer circumference side of the forward-field-of-view image, and the image is acquired as a lateral-field-of-view image.

In the present embodiment, however, the blocking portion 18a configured to mechanically block light from the object side which is incident into the ring-shaped lateral field of view is formed by the support portion 18. Further, in the present embodiment, a configuration is adopted in which lateral illuminating light emitted in the side-face direction from the lateral illuminating windows 14 side is not emitted to the support portion 18 side.

Note that, though a lateral-field-of-view image is acquired with use of the catoptric system twice in the present embodiment as a method for forming a forward-field-of-view image and a lateral-field-of-view image on one image pickup device, the lateral-field-of-view image may be acquired with the use of the catoptric system once. In the case of using the catoptric system once, an image direction of the lateral-field-of-view image may be adjusted by image processing or the like as necessary.

The lateral illuminating windows 14 are provided at a plurality of positions on an outer circumferential face near the proximal end adjoining the lateral observation window 13 on the cylindrical portion 10. In the present embodiment, the lateral illuminating windows 14 are provided at two positions on both of left and right sides in a circumferential direction, and lateral illuminating light is emitted to a whole area in the circumferential direction except the lower part side where the support portion 18 is provided.

As shown in FIG. 4, a distal end side of the light guide 44 as a light emitting member arranged along a longitudinal direction of the distal end portion 6 is extended to a vicinity of a proximal end of a cylindrical member 10a constituting the cylindrical portion 10 projecting from the distal end face of the distal end portion 6.

In the vicinity of the proximal end of the cylindrical portion 10 (on an outer circumference side of the rear lens group 43), a distal end face of the light guide 44 is arranged near its side face, and the distal end face of the light guide 44 becomes an emission end face for emitting guided light, and the light is emitted in a distal end direction. Though the emission end face is in a circular shape in the present embodiment, the emission end face is not limited to the circular shape, and different shapes, including an oval and a polygon, are also possible.

At a position which the emission end face faces, a concave portion forming a light guiding groove 45 as a groove portion configured to guide light is provided, the concave portion extending long in band shape along an outer circumference of the cylindrical-shaped side face of the cylindrical portion 10 with the position as a center. A reflecting member 46 as an illumination reflecting portion formed to face the emission end face is arranged in the concave portion, and the light guiding groove 45 provided with a reflecting portion 46a configured to reflect light is formed on an internal surface of the reflecting member 46.

As for the reflecting portion 46a on the internal surface of the light guiding groove 45 formed by the reflecting member 46 shows a concave face in a substantially semispherical shape on a longitudinal section shown in FIG. 4. Further, the semispherical-shaped concave surface of the reflecting portion 46a is formed longer than the emission end face of the light guide 44 along the circumferential direction of the cylindrical portion 10.

The reflecting portion 46a reflects light emitted toward the distal end side of the distal end portion 6 from the emission end face by the reflecting portion 46a to change a travel direction of the light to the side face direction, guides the light to a wide-range side face direction along the circumferential direction and emits the light from the lateral illuminating windows 14 to illuminate an observation field of view side (an observation target side) of the lateral observation window 13. Therefore, the light emitted to the side face direction from the light guiding groove 45 becomes lateral illuminating light.

Note that the reflecting portion 46a can be formed by providing a thin film of metal having a high reflectivity, such as aluminum, chromium, nickel chromium, silver and gold, on the internal surface of the reflecting member 46.

Thus, in the present embodiment, the reflecting member 46 is arranged in the concave portion of the light guiding groove 45 so that the light guiding groove 45 provided with the reflecting portion 46a is formed long along outer circumference of the side face of the cylindrical portion 10. Further, the emission end face of the light guide 44 as the light emitting member is arranged so as to be positioned near a central position in the circumferential direction in the reflecting member 46 or the light guiding groove 45.

Light emitted from the emission end face of the light guide 44 is reflected by the reflecting portion 46a arranged so as to form a reflecting surface around the emission end face, and illuminating light is emitted in a wide range from the lateral illuminating windows 14 provided with the light guiding groove 45 in the lateral direction.

FIG. 5 shows an example of an endoscopic image displayed on the monitor 35. An observed image 50, which is an endoscopic image displayed on a display screen 35a of the monitor 35, is a substantially rectangular image having two portions 52 and 53. The portion 52 in a circular shape at a central part is a portion to display a forward-field-of-view image, and the portion 53 in a C shape around the portion 52 at the central part is a portion to display a lateral-field-of-view image.

Note that the images displayed in the portions 52 and 53 of the endoscopic image displayed on the monitor 35 are not necessarily same as an image of an object within the forward field of view and an image of the object within the lateral field of view, respectively.

That is, the forward-field-of-view image is displayed on the display screen 35a of the monitor 35 so as to be in a substantially circular shape, and the lateral-field-of-view image is displayed on the display screen 35a so as to be in a substantially ring shape surrounding at least a part of a circumference of the forward-field-of-view image. Therefore, a wide-angle endoscopic image is displayed on the monitor 35.

The endoscopic image shown in FIG. 5 is generated from an acquired image acquired by the image pickup device 40 (FIG. 2). The observed image 50 is generated by photoelectrically converting an object image projected on the image pickup surface of the image pickup device 40 by the objective optical system provided in the distal end portion 6, and combining a forward-field-of-view image portion at a center corresponding to the portion 52 and a lateral-field-of-view image portion corresponding to the portion 53 excluding a blacked mask area 54.

(Configuration of Video Processor)

Figure 6:
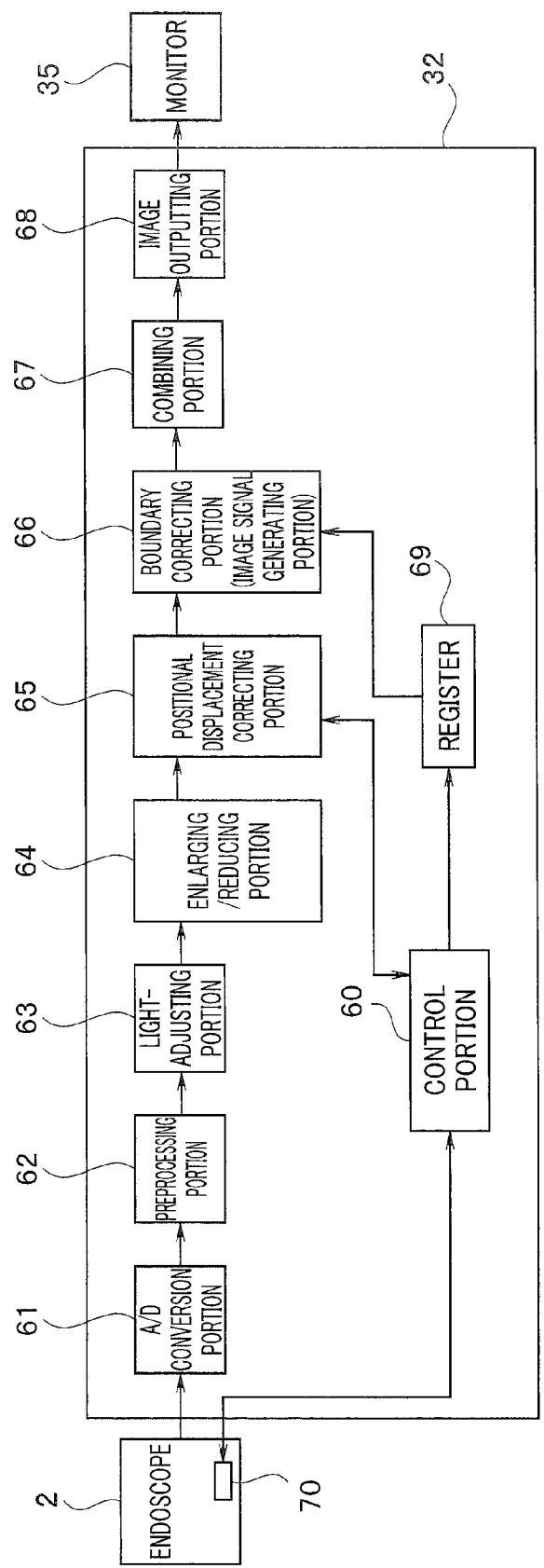
FIG. 6 is a block diagram showing a configuration of a video processor 32 according to the first embodiment of the present invention.

FIG. 6 is a block diagram showing a configuration of the video processor 32. In FIG. 6, only components related to functions of the present embodiment described below are shown, and components related to other functions such as image recording are omitted.

The video processor 32 has a control portion 60, an analog/digital converting portion (hereinafter referred to as an A/D conversion portion) 61, a preprocessing portion 62, a light-adjusting portion 63, an enlarging/reducing portion 64, a positional displacement correcting portion 65, a boundary correcting portion 66, a combining portion 67, an image outputting portion 68 and a register 69. The video processor 32 has a function of generating an image-processed image as described later.

Further, the endoscope 2 has a nonvolatile memory 70 such as a flash memory. Displacement amount data to be described later is written and stored into the memory 70 by the video processor 32 and can be read out by the video processor 32.

The control portion 60 includes a central processing unit (CPU), a ROM, a RAM and the like. The control portion 60 executes a predetermined software program in response to an instruction such as a command input by the user from an operation panel not shown, and generates or reads out various kinds of control signals or data signals to control each necessary circuit and each necessary portion in the video processor 32.

The A/D conversion portion 61 includes an A/D conversion circuit. The A/D conversion portion 61 is a circuit configured to convert an image pickup signal from the image pickup device 40 of the endoscope 2 from an analog signal to a digital signal.

The preprocessing portion 62 is a circuit configured to perform processing such as color filter conversion for an image pickup signal from the image pickup device 40 of the endoscope 2 to output a video signal.

The light-adjusting portion 63 is a circuit configured to judge brightness of an image based on the video signal and output a light adjustment control signal to the light source apparatus 31 based on a light adjustment state of the light source apparatus 31.

The enlarging/reducing portion 64 enlarges or reduces an image of the video signal outputted from the preprocessing portion 62 in accordance with the size and format of the monitor 35, and outputs a video signal of the enlarged or reduced image to the positional displacement correcting portion 65.

The positional displacement correcting portion 65 executes a process for estimating two center coordinates of a forward-field-of-view image FV and a lateral-field-of-view image SV and calculating an amount of displacement between the two estimated center coordinates. The positional displacement correcting portion 65 stores the calculated amount of displacement into the memory 70 of the endoscope 2 as well as into the register 69.

The positional displacement correcting portion 65 outputs a video signal which includes the inputted forward-field-of-view image FV and lateral-field-of-view image SV to the boundary correcting portion 66.

The boundary correcting portion 66 cuts out the forward-field-of-view image FV and the lateral-field-of-view image SV from the inputted video signal using the displacement amount data stored in the register 69 and executes a predetermined enlargement process.

Figure 7:
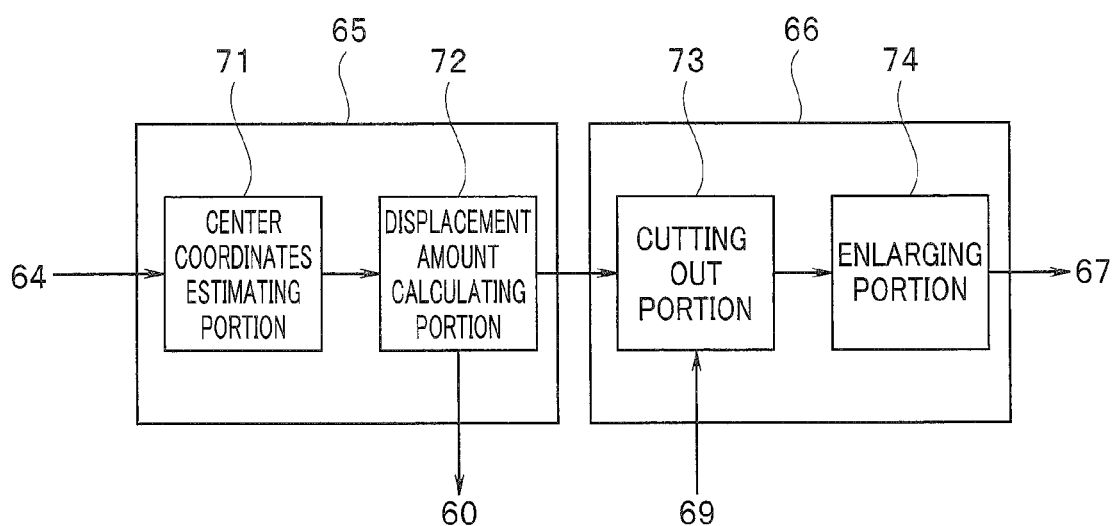
FIG. 7 is a block diagram showing configurations of a positional displacement correcting portion 65 and a boundary correcting portion 66 according to the first embodiment of the present invention.

FIG. 7 is a block diagram showing configurations of the positional displacement correcting portion 65 and the boundary correcting portion 66.

The positional displacement correcting portion 65 includes a center coordinates estimating portion 71 and a displacement amount calculating portion 72.

The center coordinates estimating portion 71 is a circuit configured to calculate and estimate an amount of displacement between positions of a center CF of a forward-field-of-view image portion FVa and a center CS of a lateral-field-of-view image portion SVa on the image pickup surface 40a of the image pickup device 40.

Since the forward-field-of-view image portion FVa and the lateral-field-of-view image portion SVa formed on the image pickup surface 40a by the optical system shown in FIG. 4 are in a circular shape and a ring shape, respectively, the center coordinates estimating portion 71 can calculate the center CF of the circular-shaped forward-field-of-view image portion FVa and the center CS of the ring-shaped lateral-field-of-view image portion SVa.

The control portion 60 reads out data from the memory 70 of the endoscope 2 to judge whether the displacement amount data exists or not. If the displacement amount data is not stored in the memory 70, the control portion 60 controls the positional displacement correcting portion 65 to cause the center coordinates estimating portion 71 and the displacement amount calculating portion 72 to operate.

As shown in FIG. 7, the boundary correcting portion 66 includes a cutting out portion 73 and an enlarging portion 74.

The cutting out portion 73 is a circuit configured to cut out the forward-field-of-view image FV of the forward-field-of-view image portion FVa and the lateral-field-of-view image SV of the lateral-field-of-view image portion SVa from an inputted video signal based on the displacement amount data read out from the register 69 and output the forward-field-of-view image FV and the lateral-field-of-view image SV to the enlarging portion 74.

The enlarging portion 74 performs an enlargement process for the cut-out forward-field-of-view image FV at a predetermined magnification and outputs the forward-field-of-view image FV to the combining portion 67.

Returning to FIG. 6, the combining portion 67 combines the forward-field-of-view image FV and the lateral-field-of-view image SV so that the respective centers CF and CV of the inputted forward-field-of-view image FV and lateral-field-of-view image SV correspond to a center C of the image pickup surface 40a and outputs an image obtained by the combination to the image outputting portion 68.

Note that the combining portion 67 also executes mask processing.

The image outputting portion 68 is a circuit as an image generating portion configured to generate an image signal which includes the forward-field-of-view image FV and the lateral-field-of-view image SV from the combining portion 67 by image processing, convert the image signal to a display signal and output the display signal to the monitor 35. That is, the image outputting portion 68 inputs an image signal from the combining portion 67, and the image outputting portion 68 generates a display signal for displaying the image signal based on the forward-field-of-view image FV and the lateral-field-of-view image SV on the monitor 35 which is a display portion.

(Operation)

Next, description will be made on an example of a procedure about a method for a process for correcting a positional displacement between a forward-field-of-view image and a lateral-field-of-view image in the video processor 32.

First, the positional displacement between a forward-field-of-view image and a lateral-field-of-view image will be described.

Figure 8:
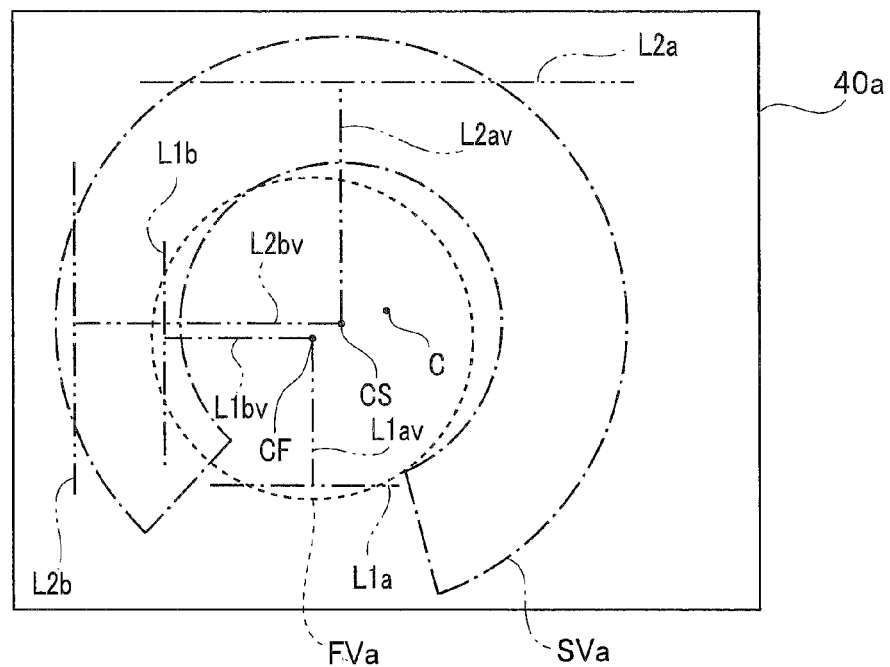
FIG. 8 is a diagram for illustrating a positional displacement between a center CF of a forward-field-of-view image portion FVa projected on an image pickup surface 40a of an image pickup device 40 and a center CS of a lateral-field-of-view image portion SVa in a center coordinates estimating portion 71 according to the first embodiment of the present invention.

FIG. 8 is a diagram for illustrating a positional displacement between a center CF of a forward-field-of-view image portion FVa projected on the image pickup surface 40a of the image pickup device 40 and a center CS of a lateral-field-of-view image portion SVa in the center coordinates estimating portion 71.

On the image pickup surface 40a of the image pickup device 40, a forward-field-of-view image portion FVa corresponding to a circular-shaped forward-field-of-view image FV by a forward-field-of-view optical system which includes the forward lens 41 of the forward observation window 12 and a lateral-field-of-view image portion SVa corresponding to a ring-shaped lateral-field-of-view image SV by a lateral-field-of-view optical system which includes the mirror lens 15 facing the lateral observation window 13 are formed.

As described above, due to variation and the like in processing accuracy of or at time of assembly of a frame for fixing each lens of the objective optical system or the image pickup device 40, the center CF of the forward-field-of-view image portion FVa (shown by a dotted line) in a circular shape and the center CS of the lateral-field-of-view image portion SVa (shown by a one-dot chain line) in a ring shape may be relatively displaced as shown in FIG. 8.

Furthermore, the center CF of the forward-field-of-view image portion FVa and the center CS of the lateral-field-of-view image portion SVa may be displaced relative to the center C of the image pickup surface 40a of the image pickup device 40. In FIG. 8, the center CF of the forward-field-of-view image portion FVa and the center CS of the lateral-field-of-view image portion SVa are also displaced relative to the center C of the image pickup surface 40a.

Therefore, the positional displacement correcting portion 65 of the video processor 32 calculates an amount of relative displacement between the center CF of the forward-field-of-view image portion FVa and the center CS of the lateral-field-of-view image portion SVa or an amount of displacement of each of the center CF of the forward-field-of-view image portion FVa and the center CS of the lateral-field-of-view image portion SVa relative to the center C of the image pickup surface 40a. Here, in the positional displacement correcting portion 65, the amount of displacement of each of the center CF of the forward-field-of-view image portion FVa and the center CS of the lateral-field-of-view image portion SVa relative to the center C of the image pickup surface 40a are calculated.

For example, at time of manufacturing the endoscope 2, a forward-field-of-view object image and a lateral-field-of-view object image are caused to be projected onto the image pickup surface 40a by picking up an appropriate object image by the distal end portion 6 of the insertion portion 4, and the positional displacement correcting portion 65 is caused to operate. A video signal of an image which includes both of the forward-field-of-view image portion FVa and the lateral-field-of-view image portion SVa is inputted to the center coordinates estimating portion 71.

Note that the center coordinates estimating portion 71 may be adapted to operate in response to a user instruction or may be adapted to automatically operate when it is judged that displacement amount data is not stored in the memory 70.

The center coordinates estimating portion 71 extracts the forward-field-of-view image portion FVa and the lateral-field-of-view image portion SVa by image processing, based on luminance values of pixels of the inputted video signal and determines the center of each of the extracted portions.

For example, the center coordinates estimating portion 71 can extract a pixel area on the image pickup surface 40$a$ corresponding to the circular-shaped forward-field-of-view image portion FVa and a pixel area on the image pickup surface 40$a$ corresponding to the ring-shaped lateral-field-of-view image portion SVa based on difference among the luminance values of the respective pixels.

In FIG. 8, coordinates of the center CF of the forward-field-of-view image portion FVa on the image pickup surface 40$a$ can be determined by assuming appropriate two straight lines L1$a$ and L1$b$ (shown by two-dot chain lines) passing through the circular-shaped forward-field-of-view image portion FVa and calculating an intersection point of perpendicular bisectors L1$av$ and L1$bv$ (shown by two-dot chain lines) for line segments of the straight lines L1$a$ and L1$b$ inside the circle, respectively.

Similarly, coordinates of the center CS of the lateral-field-of-view image portion SVa on the image pickup surface 40$a$ can be obtained by assuming appropriate two straight lines L2$a$ and L2$b$ (shown by two-dot chain lines) passing through the ring-shaped lateral-field-of-view image portion SVa and calculating an intersection point of perpendicular bisectors L2$av$ and L2$bv$ for line segments of the straight lines L2$a$ and L2$b$ inside an outside circle of the lateral-field-of-view image portion SVa, respectively.

Coordinates of the center C of the image pickup surface 40$a$ is indicated by (x0, y0); the obtained coordinates of the center CF of the forward-field-of-view image portion FVa is indicated by (xf1, yf1); and the obtained coordinates of the center CS of the lateral-field-of-view image portion SVa is indicated by (xs1, ys1).

The displacement amount calculating portion 72 calculates the amounts of displacement from the center CF of the forward-field-of-view image portion FVa and the center CS of the lateral-field-of-view image portion SVa determined by the center coordinates estimating portion 71.

An amount of displacement dfx of the center CF in an x-axis direction relative to the center C of the image pickup surface 40$a$ is indicated by an equation (1).

$$Dfx=(xf1-x0) \qquad (1)$$

Further, an amount of displacement dfy of the center CF in a y-axis direction relative to the center C of the image pickup surface 40$a$ is indicated by an equation (2).

$$Dfy=(yf1-y0) \qquad (2)$$

Similarly, an amount of displacement dsx of the center CS in the x-axis direction relative to the center C of the image pickup surface 40$a$ is indicated by an equation (3).

$$Dsx=(xs1-x0) \qquad (3)$$

Further, an amount of displacement dsy of the center CS in the y-axis direction relative to the center C of the image pickup surface 40$a$ is indicated by an equation (4).

$$Dsy=(ys1-y0) \qquad (4)$$

As described above, the center coordinates estimating portion 71 determines the center CF of the forward-field-of-view image portion FVa and the center CS of the lateral-field-of-view image portion SVa, and the displacement amount calculating portion 72 can calculate the amounts of displacement from the coordinates of the center CF of the forward-field-of-view image portion FVa and the center CS of the lateral-field-of-view image portion SVa determined by the center coordinates estimating portion 71.

The control portion 60 writes the calculated displacement amount data into the memory 70 and the register 69.

As a result, after manufacture of the endoscope 2 or at time of using the endoscope 2 for the first time, the video processor 32 can read out the displacement amount data from the memory 70 if the endoscope system 1 has been powered on and the center coordinates estimating portion 71 has operated before, and, therefore, the control portion 60 writes the read-out displacement amount data to the register 69. That is, until a positional relationship detection signal is updated, the boundary correcting portion 66 generates an image signal in which arrangement of the forward-field-of-view image FV and the lateral-field-of-view image is changed based on positional relationship detection information stored in the memory 70.

Further, if the endoscope system 1 has not been powered on, and the center coordinates estimating portion 71 has not operated after manufacture of the endoscope 2, the control portion 60 cannot read out the displacement amount data from the memory 70 when the endoscope system 1 is powered on. In such a case, the control portion 60 causes the center coordinates estimating portion 71 and the displacement amount calculating portion 72 to operate to perform calculation of the equations (1) to (4) described above, calculates the displacement amount data Dfx, Dfy, Dsx and Dsy, stores the displacement amount data Dfx, Dfy, Dsx and Dsy into the memory 70 and writes the displacement amount data Dfx, Dfy, Dsx and Dsy to the register 69.

As described above, the displacement amount data Dfx, Dfy, Dsx and Dsy are information indicating a positional relationship between the forward-field-of-view image portion FVa and the lateral-field-of-view image portion SVa. The memory 70 is a storage portion configured to store positional relationship detection information.

Therefore, the positional displacement correcting portion 65 constitutes an object image position detecting portion configured to detect a positional relationship between the forward-field-of-view image portion FVa, which is a first portion where a front-direction object image is formed, and the lateral-field-of-view image portion SVa, which is a second portion where a lateral-direction object image is formed, in the image pickup device 40 configured to pick up a forward object image and a lateral object image and generate positional relationship detection information.

Here, the positional relationship is indicated by the amount of displacement of the portion FVa relative to the center C of the image pickup surface 40$a$, which is a predetermined position of an image acquired by the image pickup device 40, and the amount of displacement of the portion SVa relative to the center C of the image pickup surface 40$a$. Therefore, the positional relationship detection information includes the two amounts of displacement.

The displacement amount calculating portion 72 executes the displacement amount calculation process described above and outputs a video signal to the cutting out portion 73.

Figure 9:
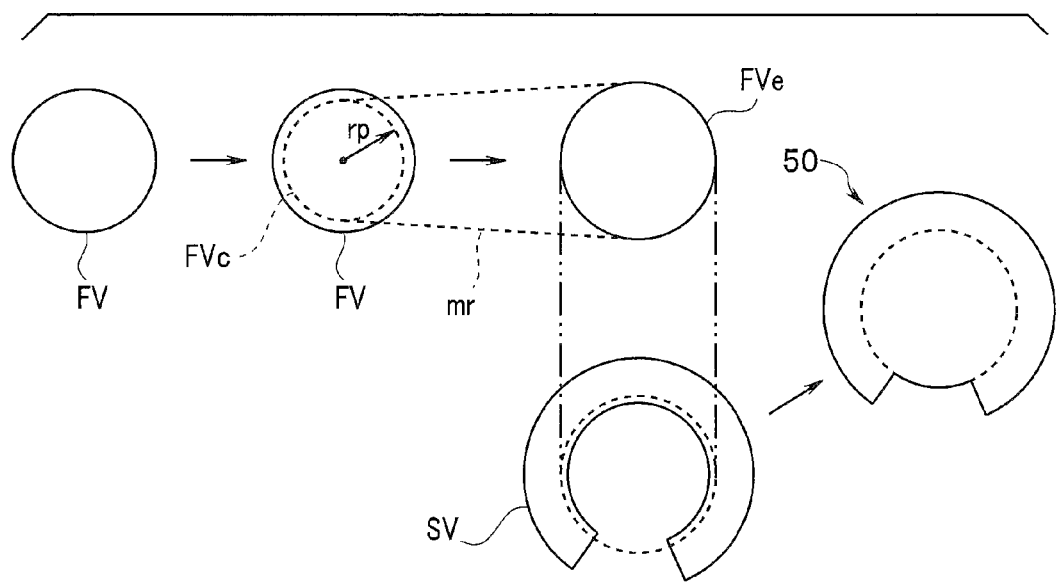
FIG. 9 is a diagram for illustrating a process by a cutting out portion 73, an enlarging portion 74 and a combining portion 67 according to the first embodiment of the present invention.

FIG. 9 is a diagram for illustrating a process by the cutting out portion 73, the enlarging portion 74 and the combining portion 67.

The cutting out portion 73 cuts out the forward-field-of-view image FV and the lateral-field-of-view image SV from the inputted video signal based on the displacement amount data Dfx, Dfy, Dsx and Dsy, and, furthermore, cuts out a central part image FVc with a predetermined radius rp from the forward-field-of-view image FV as shown in FIG. 9. As a result, an image of a circumferential part of the forward-field-of-view image FV is not used for an observed image.

The enlarging portion 74 enlarges the central part image FVc at a predetermined magnification mr to generate an enlarged central part image FVe. The magnification mr is of such a value that a radius of the enlarged central part image FVe which has been enlarged is larger than a diameter of the forward-field-of-view image FV cut out by the cutting out portion 73.

The combining portion 67 combines the enlarged central part image FVe and the lateral-field-of-view image SV, performs necessary mask processing, and outputs an image to the image outputting portion 68.

As a result, an observed image 50 obtained by the combination becomes an image in which an inside peripheral portion of the lateral-field-of-view image SV is covered and hidden by the enlarged central part image FVe, and a boundary area between the forward-field-of-view image FV and the lateral-field-of-view image SV becomes a smooth image area in the observed image 50 obtained by combination.

Therefore, the boundary correcting portion 66 constitutes an image signal generating portion configured to generate an image signal in which the forward-field-of-view image FV and the lateral-field-of-view image SV are arranged with the center CF, which is a reference position provided in the forward-field-of-view image portion FVa, and the center CS, which is a reference position provided in the lateral-field-of-view image portion SVa, caused to correspond to each other, by image processing based on the positional relationship detection information.

Note that, though the boundary correcting portion 66 causes positions of the forward-field-of-view image FV and the lateral-field-of-view image SV to change so that both of the center position of the object image in the forward-field-of-view image portion FVa and the center position of the object image in the lateral-field-of-view image portion SVa correspond to the center C of the image pickup surface 40a here, the boundary correcting portion 66 may perform a process for causing the position of at least one of the forward-field-of-view image FV and the lateral-field-of-view image SV to change so as to correct displacement between coordinates of the center position of the object image in the forward-field-of-view image portion FVa and coordinates of the center position of the object image in the lateral-field-of-view image portion SVa. In that case, the boundary correcting portion 66 causes arrangement of one of the forward-field-of-view image portion FVa and the lateral-field-of-view image portion SVa to change in accordance with the position of the other between the forward-field-of-view image portion FVa and the lateral-field-of-view image portion SVa, based on the positional relationship detection information indicating a position relationship between the forward-field-of-view image portion FVa and the lateral-field-of-view image portion SVa.

Furthermore, note that coordinates of the center position of the object image may be coordinates of a pixel on the monitor 35, which is a display portion where the forward-field-of-view image FV and the lateral-field-of-view image SV are displayed, and the amount of displacement may be converted to and indicated by the number of pixels on the coordinates.

Note that, since sizes of the forward-field-of-view image FV and the lateral-field-of-view image SV differ for each endoscope 2, information about the predetermined radius rp and the predetermined magnification mr may be stored in the memory 70 of the endoscope 2 in advance, or the control portion 60 may read out the information from the memory 70 and store the information into the register 69 when the endoscope 2 is connected to the video processor 32 and powered on. The boundary correcting portion 66 reads out the information about the predetermined radius rp and the predetermined magnification mr from the register 69 and performs cut-out and enlargement of the central part image FVc. As a result, the boundary between the forward-field-of-view image FV and the lateral-field-of-view image SV becomes inconspicuous in the observed image 50 displayed on the monitor 35.

Note that common smoothing processing may be performed for the boundary area between the combined forward-field-of-view image FV and lateral-field-of-view image SV.

As described above, when the endoscope 2 is connected to the video processor 32, and a process by the positional displacement correcting portion 65 is executed once, displacement amount data is stored into the memory 70. After that, when the endoscope 2 and the video processor 32 are connected and powered on, the process by the positional displacement correcting portion 65 is not executed, and the control portion 60 reads out the displacement amount data from the memory 70, and the boundary correcting portion 66 performs boundary correction based on the displacement amount data which has been read out and stored into the register 69.

The process by the positional displacement correcting portion 65 may be executed when the endoscope 2 is manufactured. Even if the process is not executed at the time of manufacture, the process is executed when the endoscope 2 is connected to the video processor 32 for the first time.

Furthermore, the process by the positional displacement correcting portion 65 may be adapted to be executed when the endoscope 2 is repaired.

As described above, according to the embodiment described above, it is possible to provide an endoscope system which, even if a displacement between optical systems for a forward-field-of-view image FV and a lateral-field-of-view image SV exists due to variation and the like in the processing accuracy of or at the time of assembly of the frame for fixing the lens of the objective optical system or the image pickup device, does not cause the user to feel unnatural from the forward-field-of-view image FV and the lateral-field-of-view image SV simultaneously displayed on the monitor 35.

Furthermore, since centers of the forward-field-of-view image FV and the lateral-field-of-view image SV correspond to each other, a boundary correction process can be performed accurately.

Second Embodiment

The endoscope system 1 of the first embodiment has the endoscope 2 which obtains a forward-field-of-view image and a lateral-field-of-view image arranged surrounding the forward-field-of-view image with one image pickup device. An endoscope system 1A of a second embodiment, however, has an endoscope 2A which obtains a forward-field-of-view image and a lateral-field-of-view image with separate image pickup devices.

Note that a configuration of the endoscope system 1A of the second embodiment is substantially same as the endoscope system 1 described in the first embodiment and shown in FIG. 1. Same components will be given same reference numerals, and description of the components will be omitted.

(System Configuration)

Figure 10:
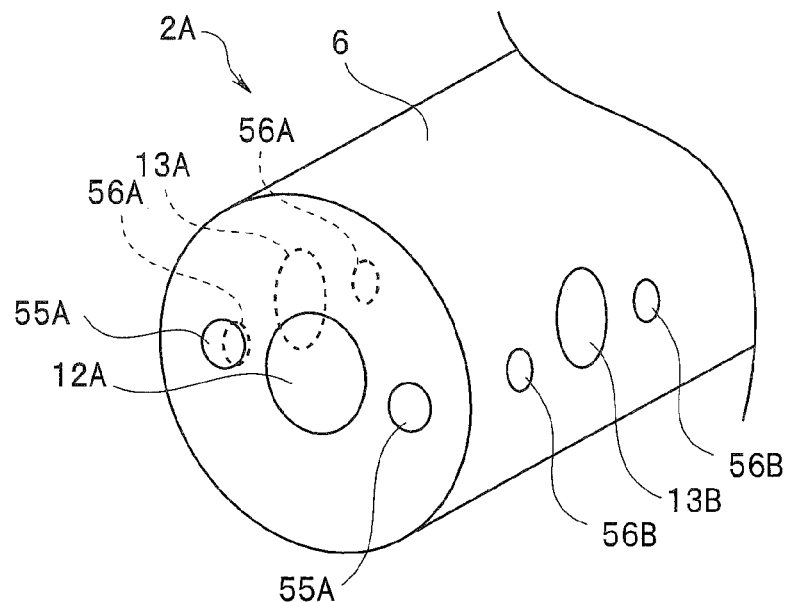
FIG. 10 is a simplified schematic perspective view of a distal end portion 6 of an endoscope 2A according to a second embodiment of the present invention.
Figure 11:
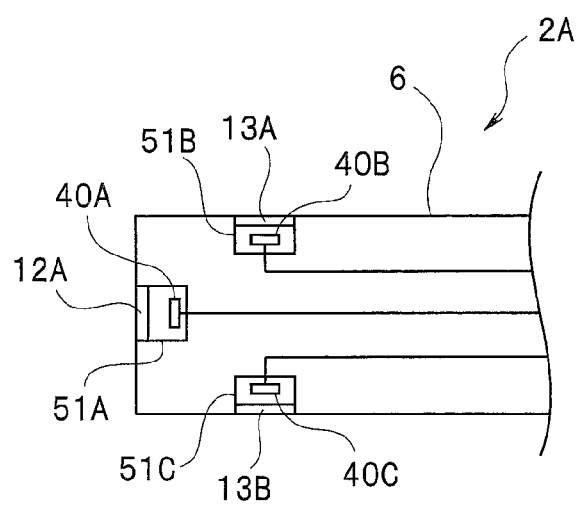
FIG. 11 is a schematic configuration diagram showing an internal configuration of the distal end portion 6 according to the second embodiment of the present invention.

FIG. 10 is a simplified schematic perspective view of the distal end portion 6 of the endoscope 2A of the present embodiment. FIG. 11 is a schematic configuration diagram showing an internal configuration of the distal end portion 6. In FIGS. 10 and 11, components such as a treatment instrument opening and cleaning nozzles are omitted.

As shown in FIG. 11, an image pickup unit 51A for forward field of view is provided on the distal end face of the cylindrical-shaped distal end portion 6 of the endoscope 2A. On a side face of the distal end portion 6 of the endoscope 2A, two image pickup units 51B and 51C for lateral field of view are provided. The three image pickup units 51A, 51B and 51C have image pickup devices 40A, 40B and 40C, respectively, and each image pickup unit is provided with an objective optical system not shown.

The respective image pickup units 51A, 51B and 51C are arranged on back face sides of a forward observation window 12A and lateral observation windows 13A and 13B, respectively. The image pickup units 51A, 51B and 51C receive reflected light from an object illuminated by illuminating light emitted from two illuminating windows 55A, two illuminating windows 56A and two illuminating windows 56B and output image pickup signals.

The three image pickup signals from the three image pickup devices 40A, 40B and 40C are inputted to an A/D conversion portion 61A (FIG. 12) to be described later.

The forward observation window 12A is arranged on the distal end portion 6 of the insertion portion 4, facing the direction in which the insertion portion 4 is inserted. The lateral observation windows 13A and 13B are arranged on a side face portion of the insertion portion 4 at substantially equal angles in the circumferential direction of the distal end portion 6, facing the outer diameter direction of the insertion portion 4. The lateral observation windows 13A and 13B are arranged on the distal end portion 6 so as to face mutually opposite directions.

The image pickup devices 40A, 40B and 40C of the image pickup units 51A, 51B and 51C are electrically connected to the video processor 32A (FIG. 12) and controlled by the video processor 32A to output image pickup signals to the video processor 32A. Each of the image pickup units 51A, 51B and 51C is an image pickup portion configured to photoelectrically convert an object image.

That is, the forward observation window 12A is provided on the insertion portion 4 and constitutes a first image acquiring portion configured to acquire an image of a first object image from a forward direction, which is a first direction, and each of the lateral observation windows 13A and 13B is provided on the insertion portion 4 and constitutes a second image acquiring portion configured to acquire a second object image from a lateral direction, which is a second direction different from the forward direction. In other words, the first object image is an object image in the first direction including the forward direction of the insertion portion substantially parallel to the longitudinal direction of the insertion portion 4, and the second object image is an object image in the second direction including the lateral direction of the insertion portion substantially orthogonal to the longitudinal direction of the insertion portion 4. Furthermore, the forward observation window 12A is a forward image acquiring portion configured to acquire an object image in a direction including the forward direction of the insertion portion, and the lateral observation windows 13A and 13B are lateral image acquiring portions configured to acquire an object image in a direction including the lateral direction of the insertion portion.

The image pickup unit 51A is an image pickup portion configured to photoelectrically convert an image from the forward observation window 12A, and the image pickup units 51B and 51C are image pickup portions configured to photoelectrically convert two images from the lateral observation windows 13A and 13B, respectively. That is, the image pickup unit 51A is an image pickup portion configured to pick up an object image for acquiring a forward-field-of-view image, and the image pickup units 51B and 51C are image pickup portions configured to pick up an object image for acquiring a lateral-field-of-view image, respectively. An image signal of the forward-field-of-view image is generated from an image obtained by the image pickup unit 51A, and image signals of the two lateral-field-of-view images are generated from images obtained by the image pickup units 51B and 51C.

On a back side of each of the illuminating windows 55A, 56A and 56B, a distal end portion of a light guide not shown or a luminous body such as a light emitting diode (LED) is arranged in the distal end portion 6.

(Configuration of Video Processor)

Figure 12:
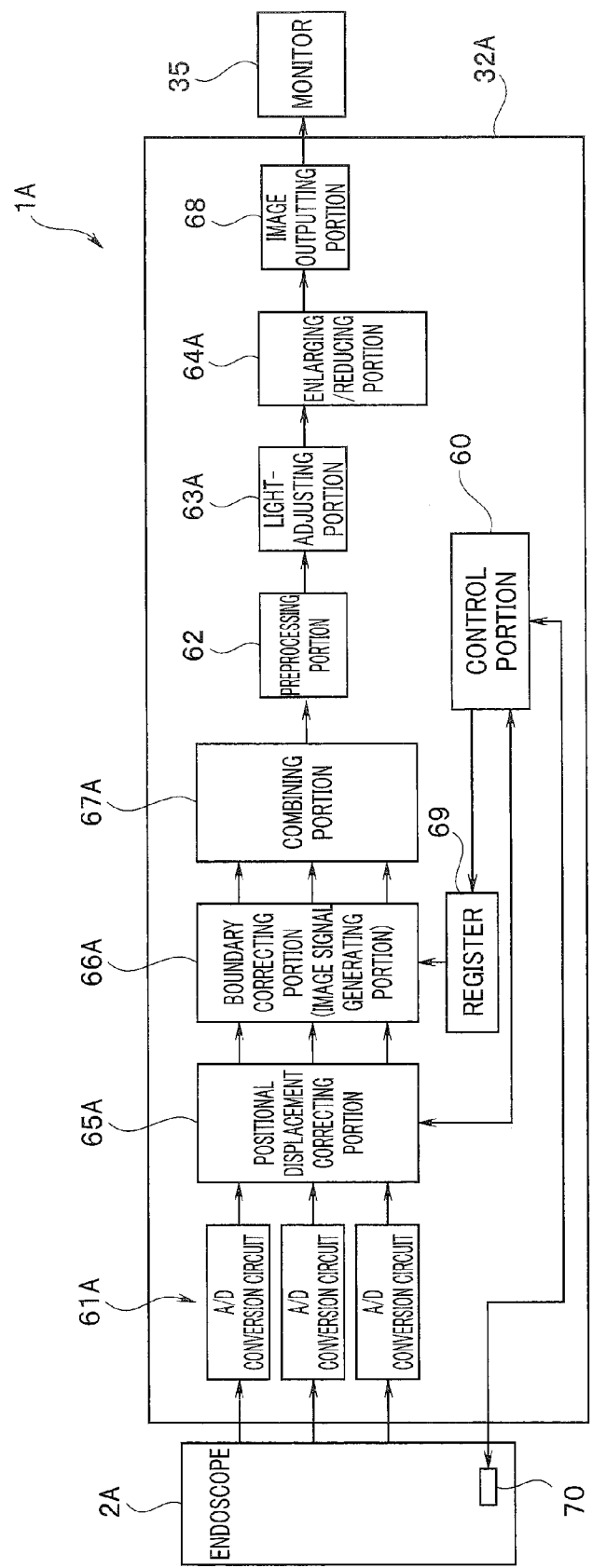
FIG. 12 is a block diagram showing a configuration of a video processor 32A according to the second embodiment of the present invention.

FIG. 12 is a block diagram showing a configuration of the video processor 32A according to the present embodiment. Note that, in FIG. 12, only components related to functions of the present embodiment described below are shown, and components related to other functions such as image recording are omitted. Further, in the configuration of the video processor 32A of FIG. 12, same components as components of the video processor 32 of the first embodiment will be given same reference numerals, and description of the components will be omitted.

As shown in FIG. 12, the video processor 32A has the control portion 60, the A/D conversion portion 61A, a positional displacement correcting portion 65A, a boundary correcting portion 66A, a combining portion 67A, the pre-processing portion 62, a light-adjusting portion 63A, an enlarging/reducing portion 64A, the image outputting portion 68, and the register 69.

The A/D conversion portion 61A includes three A/D conversion circuits. The respective A/D conversion circuits are circuits configured to convert image pickup signals from the respective image pickup devices 40A, 40B and 40C of the endoscope 2A from analog signals to digital signals.

The positional displacement correcting portion 65A has the center coordinates estimating portion 71 and the displacement amount calculating portion 72 shown in FIG. 7 and executes a process for calculating an amount of displacement of each of three images obtained by the three image pickup devices 40A, 40B and 40C. The positional displacement correcting portion 65A stores three pieces of displacement amount data calculated for the three image pickup devices 40A, 40B and 40C into the memory 70 of the endoscope 2 as well as into the register 69.

The positional displacement correcting portion 65A outputs video signals of the three inputted images to the boundary correcting portion 66A.

The boundary correcting portion 66A has the cutting out portion 73 and the enlarging portion 74 shown in FIG. 7, and executes an image cut-out process and a predetermined enlargement process for each of the inputted video signal using the three pieces of displacement amount data stored in the register 69.

The combining portion 67A combines three endoscopic images in order to arrange and display the endoscopic images on a screen of the monitor 35 and outputs an image obtained by the combination to the preprocessing portion 62.

Note that, though one monitor 35 is provided in the present embodiment, a forward-field-of-view image and two lateral-field-of-view images may be displayed on separate monitors, respectively. In such a case, the combining portion 67A is unnecessary.

The light-adjusting portion 63A is a circuit configured to judge brightness of each of images in the video signals received from the preprocessing portion 62 and output a light adjustment control signal to the light source apparatus 31 based on a light adjustment state of the light source apparatus 31.

The enlarging/reducing portion 64A enlarges or reduces the images of the video signals from the preprocessing portion 62 in accordance with the size and format of the monitor 35, and outputs video signals of the enlarged or reduced images to the image outputting portion 68.

Figure 13:
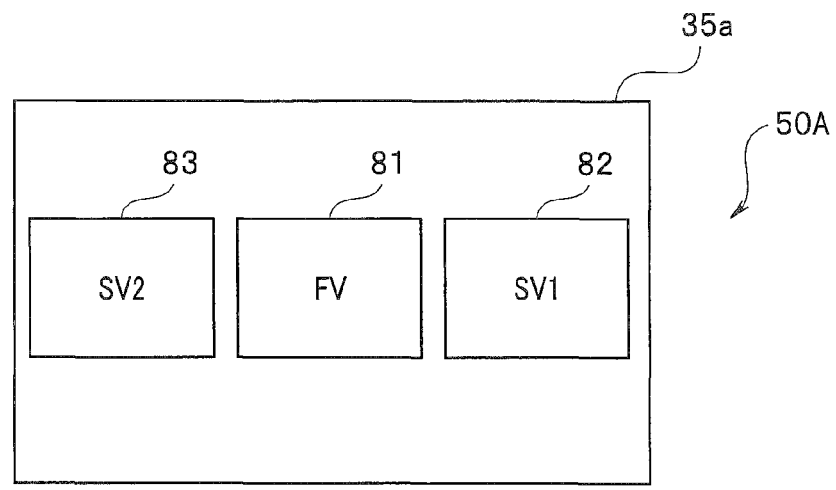
FIG. 13 is a diagram showing an example of an observed image displayed on a monitor 35 by image processing by the video processor 32A of an endoscope system 1A according to the second embodiment of the present invention.

FIG. 13 is a diagram showing an example of an observed image displayed on the monitor 35 by image processing by the video processor 32A of the endoscope system 1A.

As shown in FIG. 13, an observed image 50A, which is an endoscopic image displayed on the display screen 35a of the monitor 35, includes three image display portions 81, 82 and 83. Each of the image display portions 81, 82 and 83 is a substantially rectangular image. A forward-field-of-view image FV is displayed at a center; a right-side lateral-field-of-view image SV1 is displayed on a right side; and a left-side lateral-field-of-view image SV2 is displayed on a left side. That is, the image outputting portion 68 causes the two lateral-field-of-view images SV1 and SV2 to be displayed on the monitor 35, which is a display portion, so that the lateral-field-of-view images SV1 and SV2 are positioned next to the forward-field-of-view image FV.

The plurality of lateral-field-of-view images exist. Here, at least on both sides of the forward-field-of-view image FV, a plurality of lateral-field-of-view images, here, the two lateral-field-of-view images SV1 and SV2 are arranged.

The forward-field-of-view image FV is generated from an image acquired by the image pickup device 40A (FIG. 11) of the image pickup unit 51A. The image of the image display portion 82 is generated from an image acquired by the image pickup device 40B (FIG. 11) of the image pickup unit 51B. The image of the image display portion 83 is generated from an image acquired by the image pickup device 40C (FIG. 11) of the image pickup unit 51C.

(Operation)

Next, description will be made on an example of a procedure about a method for a process for correcting a positional displacement among the forward-field-of-view image FV and the two lateral-field-of-view images SV1 and SV2 in the video processor 32A.

In the case of the present embodiment, the image pickup unit 51A and the two image pickup units 51B and 51C are arranged on the distal end portion 6 so that the image pickup unit 51A picks up an image of the forward direction of the distal end portion 6, and the image pickup units 51B and 51C pick up images of the lateral direction of the distal end portion 6 in mutually opposite directions. Therefore, in some cases, each of central axes of the three image pickup devices 40A, 40B and 40C is displaced relative to a predetermined optical axis in a horizontal or vertical direction due to variation and the like in processing accuracy of or at time of assembly of a frame for fixing each lens of objective optical systems or each of the image pickup devices 40A, 40B and 40C of the respective image pickup units 51A, 51B and 51C.

Therefore, in the present embodiment, the positional displacement correcting portion 65A configured to execute a positional displacement correction process calculates, for the three images, an amount of displacement from a predetermined position by image processing.

In the present embodiment also, the positional displacement correcting portion 65A is controlled by the control portion 60 so as to operate when the endoscope 2A is connected to the video processor 32A and powered on, at manufacture of the endoscope 2A or at time of using the endoscope 2A for the first time, similarly to the first embodiment.

At that time, the positional displacement correction process is caused to be executed in a state that a predetermined cap 91 is put on the distal end portion 6.

Figure 14:
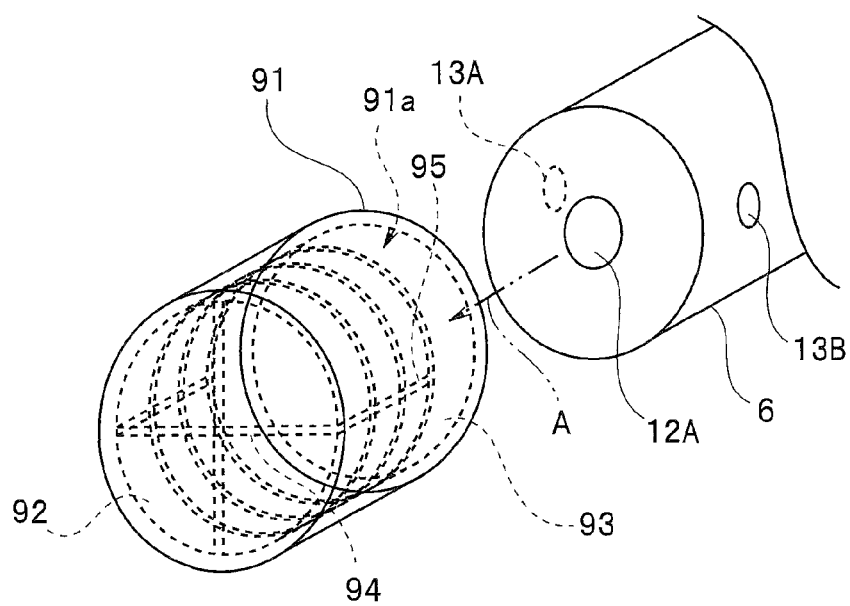
FIG. 14 is a perspective view showing a configuration of a cap 91 according to the second embodiment of the present invention.

FIG. 14 is a perspective view showing a configuration of the cap 91.

The cap 91 is a member having a cylindrical shape with a distal end portion closed. The cap 91 has an opening 91a through which the distal end portion 6 of the insertion portion 4 can be inserted from a proximal end side of the cap 91.

On an internal wall surface 92 and an internal circumferential surface 93 on a distal end side of the cap 91, predetermined reference figures are provided by printing or the like.

Here, the reference image provided on the internal wall surface 92 on the distal end side of the cap 91 is cross lines 94 extending in an upward-and-downward direction and a left-and-right direction, respectively. The reference image provided on the internal circumferential surface 93 of the cap 91 is grid lines 95 extending in the upward-and-downward direction and the left-and-right direction, respectively.

As shown by a two-dot chain line arrow A, the user inserts the distal end portion 6 into the cap 91 from the opening 91a, puts the cap 91 on the distal end portion 6, and then causes the positional displacement correcting portion 65A to operate.

Note that, in order that each of the image pickup devices 40A, 40B and 40C picks up an image of the cross lines 94 and the grid lines 95 in the cap 91 around an axis of the distal end portion 6 at a predetermined angle, reference position marks (not shown) or the like for positioning are provided on the cap 91 and the distal end portion 6.

That is, in a state that the cap 91 is put on the distal end portion 6 with the reference position marks (not shown) on the cap 91 and the distal end portion 6 aligned with each other, a vertical direction of the image pickup device 40A and a direction of a vertical line of the cross lines 94 correspond to each other, and a horizontal direction of the image pickup device 40A and a direction of a horizontal line of the cross lines 94 correspond to each other in an image obtained when the image pickup device 40A picks up an image of the cross lines 94 in the cap 91.

In a state that the cap 91 is put on the distal end portion 6 with the reference position marks (not shown) on the cap 91 and the distal end portion 6 aligned with each other, each of vertical directions of the image pickup devices 40B and 40C and a direction of a vertical line of the grid lines 95 correspond to each other in the image obtained when the image pickup device 40A picks up an image of the cross lines 94 in the cap 91.

Figure 15:
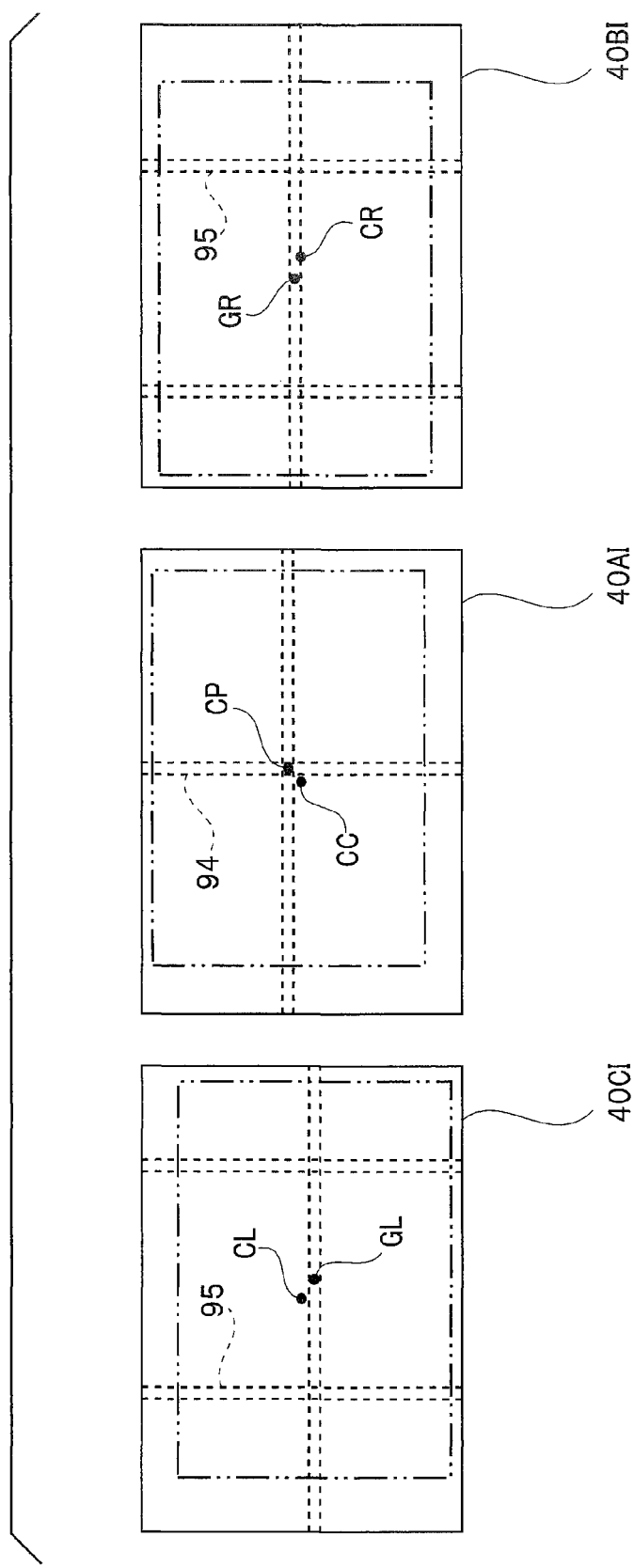
FIG. 15 is a diagram for illustrating displacements of object images formed on image pickup surfaces of respective image pickup devices 40A, 40B and 40C according to the second embodiment of the present invention.

FIG. 15 is a diagram for illustrating displacements of object images formed on image pickup surfaces of the respective image pickup devices 40A, 40B and 40C. In FIG. 15, areas 40AI, 40BI and 40CI indicate ranges of images obtained on the image pickup surfaces of the image pickup devices 40A, 40B and 40C, respectively.

The image obtained by each image pickup device is obtained by cutting out an area with a predetermined size in an image pickup signal of the image pickup device. A reference point for cut-out is a center point of each image (hereinafter referred to as an image center point).

A predetermined area is cut out from the area 40AI obtained by the image pickup device 40A with an image center point CC as a reference; a predetermined area is cut out from the area 40BI obtained by the image pickup device 40B with an image center point CR as a reference; and a predetermined area is cut out from the area 40CI obtained by the image pickup device 40C with an image center point CL as a reference.

At time of the positional displacement correction process, an image of the cross lines 94 provided on the internal wall surface 92 on the distal end side of the cap 91 is included in the area 40AI obtained by the image pickup device 40A. An image of the grid lines 95 provided on the internal circumferential surface 93 in the cap 91 is included in the areas 40BI and 40CI obtained by the image pickup devices 40B and 40C.

If the processing accuracy of the frame for fixing each lens of the objective optical system or each image pickup device of each image pickup unit is complete, and does not have variation and the like at the time of assembly, the image center point CC corresponds to an intersection point CP as a center point of the cross lines 94 in the area 40AI. Furthermore, the image center points CR and CL of the image pickup devices 40B and 40C correspond to center points GR and GL of the grid lines 95, respectively.

As shown in FIG. 15, however, though the vertical line and horizontal line of the cross lines 94 are parallel to a Y direction and an X direction, respectively, in the area 40AI obtained by the image pickup device 40A, the image center point CC passing through the central axis of the image pickup device 40A and the intersection point CP as the center point of the cross lines 94 do not correspond to each other if variation and the like in the processing accuracy of or at the time of assembly of the frame for fixing each lens of the objective optical system or the image pickup device of each image pickup unit exist.

In the area 40BI obtained by the image pickup device 40B also, though the vertical line and horizontal line of the grid lines 95 are parallel to the Y direction and the X direction, respectively, the image center point CR passing through a central axis of the image pickup device 40B and the center point GR of the grid lines 95 do not correspond to each other for a similar reason. In the image obtained by the image pickup device 40C also, though the vertical line and horizontal line of the grid lines 95 are parallel to the Y direction and the X direction, respectively, the image center point CL passing through a central axis of the image pickup device 40C and the center point GL of the grid lines 95 do not correspond to each other for a similar reason.

Though the intersection point CP of the cross lines 94, the points GR and GL at the center on the horizontal line between the two vertical lines of the grid lines 95, and the respective image center points CC, CR and CL are used to determine the amount of displacement here, points at other positions may be used.

The center coordinates estimating portion 71 of the positional displacement correcting portion 65A calculates and estimates the center points of the reference figures (the cross lines 94 and the grid lines 95) in each image (hereinafter referred to as reference figure center points). More specifically, the center coordinates estimating portion 71 determines, in the area 40AI, a position of the intersection point CP of the cross lines 94 on the image pickup surface 40a, and determines, in the area 40BI and the image CI, positions of the center points GR and GL of the grid lines 95 on the image pickup surface 40a, respectively, by image processing.

The displacement amount calculating portion 72 calculates an amount of displacement of the reference figure center point relative to the image center point of each image. The control portion 60 stores the calculated displacement amount data into the memory 70 of the endoscope 2A as well as into the register 69.

The displacement amount data of the reference figure center point relative to the image center point of each image is information showing a positional relationship among the areas 40AI, 40BI and 40CI. More specifically, the positional displacement correcting portion 65A calculates, for the area 40AI, an amount of displacement $D1x$ in an X axis direction and an amount of displacement $D1y$ in a Y axis direction between the image center point CC and the reference figure center point CP of the cross lines 94 on the image pickup surface 40a of the image pickup device 40A.

Similarly, the positional displacement correcting portion 65A calculates, for the area 40BI, an amount of displacement $D2x$ in the X axis direction and an amount of displacement $D2y$ in the Y axis direction between the image center point CR and the reference figure center point GR of the grid lines 95 on the image pickup surface 40a of the image pickup device 40B.

Similarly, the positional displacement correcting portion 65A calculates, for the area 40CI, an amount of displacement $D3x$ in the X axis direction and an amount of displacement $D3y$ in the Y axis direction between the image center point CL and the reference figure center point GL of the grid lines 95 on the image pickup surface 40a of the image pickup device 40C.

Therefore, the positional displacement correcting portion 65 constitutes an object image position detecting portion configured to detect a positional relationship among the area 40AI where a forward object image is formed, the area 40BI where a first lateral object image is formed, and the area 40CI where a second lateral object image is formed, in the image pickup devices 40A, 40B and 40C configured to pick up a forward object image and two lateral object images and generate positional relationship detection information.

The boundary correcting portion 66A cuts out images from the respective images so that the three reference figure center points CP, GR and GL correspond to one another, based on the three pieces of displacement amount data stored in the register 69, and executes an enlargement process so that the respective images are of a same size.

The cutting out portion 73 of the boundary correcting portion 66A cuts out the respective images, for example, with the reference figure center point CP as a center of image cut-out for the area 40AI, with the reference figure center point CR as a center of image cut-out for the area 40BI, and with the reference figure center point CL as a center of image cut-out for the area 40CI.

As a result, in FIG. 15, an area indicated by a two-dot chain line is cut out from each of the areas 40AI, BI and CI.

Since in some cases, sizes of the three images cut out by the cutting out portion 73 are different from one another, the enlarging portion 74 of the boundary correcting portion 66A executes an enlargement process or a reduction process for each of the images so that the sizes of the three images become the same, and outputs the images to the combining portion 67A.

That is, the boundary correcting portion 66A constitutes an image signal generating portion configured to generate an image signal in which the forward-field-of-view image FV and the two lateral-field-of-view images SV1 and SV2 are arranged such that the reference figure center point CP, which is a reference position provided in the area 40AI, and the reference figure center points GR and GL, which are second reference positions provided in the areas 40BI and 40CI, are adjusted to correspond to one another based on the positional relationship detection information.

In other words, the boundary correcting portion 66A generates an image signal in which arrangement of the forward-field-of-view image FV and the two lateral-field-of-view images SV1 and SV2 is changed so that coordinates of the reference figure center point CP, which is a reference position provided in the area 40AI, and coordinates of the reference figure center points GR and GL provided in at least two areas 40BI and 40CI, respectively, are adjusted to correspond to one another.

Note that, though the boundary correcting portion 66A causes positions of cutting out the forward-field-of-view image FV and the lateral-field-of-view images SV1 and SV2 to change so that the reference figure center points CP, GR and GL of the respective areas 40AI, 40BI and 40CI correspond to one another here, the boundary correcting portion 66A may perform a process for changing the positions of the forward-field-of-view image FV and at least one of the lateral-field-of-view images SV so that a displacement between a straight line extending in a vertical or horizontal direction from coordinates of a predetermined position of a reference figure in a forward-field-of-view image portion FVa and a straight line extending in the vertical or horizontal direction from coordinates of a predetermined position of a reference figure in a lateral-field-of-view image portion SVa is corrected in each of the areas 40AI, 40BI and 40CI. In that case, the boundary correcting portion 66A causes arrangement of two among the three areas to change in accordance with the position of the other one area based on the positional relationship detection information showing the positional relationship among respective areas 40AI, 40BI and 40CI.

Furthermore, note that the coordinates of each reference image may be coordinates of a pixel on the monitor 35, which is a display portion where the forward-field-of-view image FV and the lateral-field-of-view images SV1 and SV2 are displayed, and the amount of displacement may be converted to and indicated by the number of pixels on the coordinates.

Figure 16:
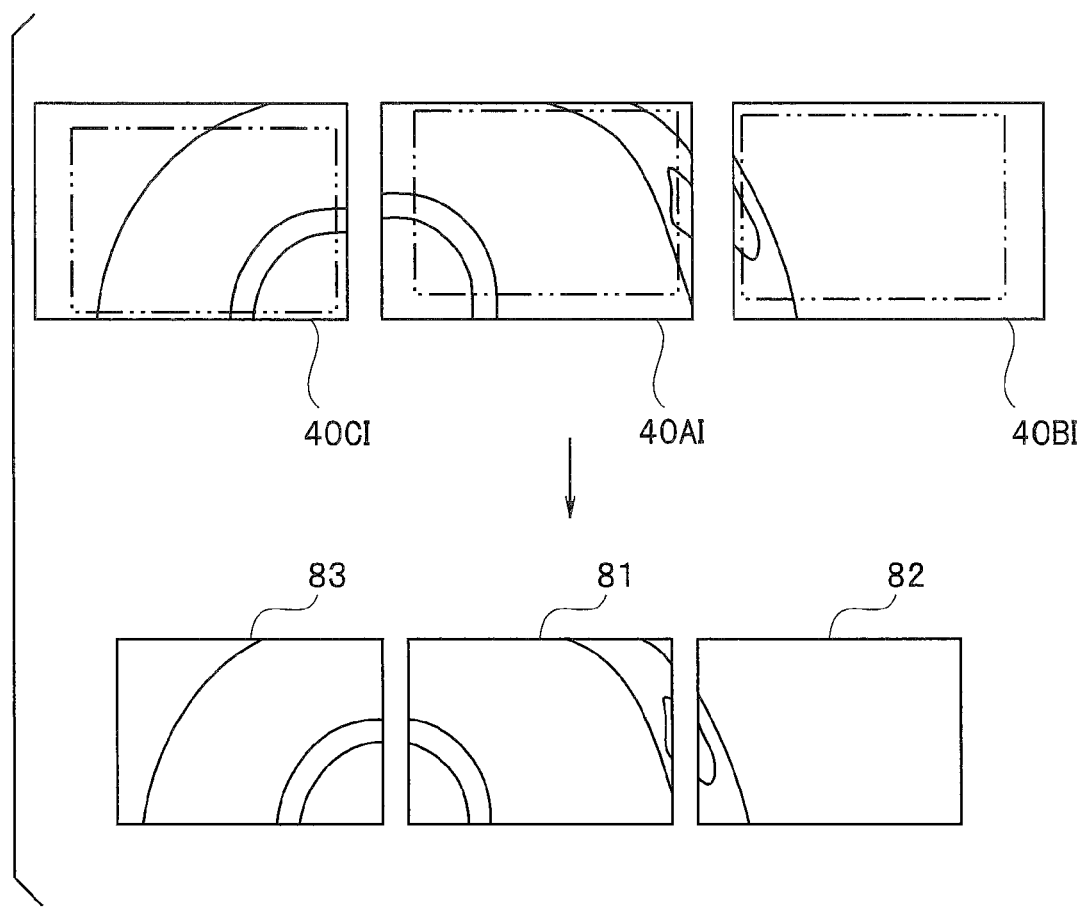
FIG. 16 is a diagram for illustrating an example in which positional displacement correction according to the second embodiment of the present invention has been performed.

FIG. 16 is a diagram for illustrating an example in which positional displacement correction according to the present embodiment has been performed.

In FIG. 16, an upper part shows the three respective areas 40AI, 40BI and 40CI, and the image center point in each of the areas 40AI, 40BI and 40CI is displaced relative to a predetermined position in a case where no variation and the like in the processing accuracy or at the time of assembly exists.

By performing the positional displacement correction process as described above, however, the cut out areas are changed, and three endoscopic images are displayed on the monitor 35 as shown in a lower part, so that the user can see the three endoscopic images without feeling unnatural.

Note that, though lateral-direction positional displacement adjustment is performed based on an amount of displacement of a reference figure center point relative to an image center point in each of the areas 40AI, 40BI and 40CI, the lateral-direction positional displacement adjustment may be performed so that a distance from the reference figure center point CP in the image display portion 81 to the reference figure center point CR in the image display portion 82 and a distance from the reference figure center point CP in the image display portion 81 to the reference figure center point CL in the image display portion 83 on the display screen 35a may be equal.

In the present embodiment also, the control portion 60 reads out data from the memory 70 of the endoscope 2 to judge whether displacement amount data exists or not. If the displacement amount data is not stored in the memory 70, the control portion 60 causes the center coordinates estimating portion 71 and the displacement amount calculating portion 72 to operate and performs control to execute the positional displacement correction process.

Note that, in the present embodiment also, the process by the positional displacement correcting portion 65 may be adapted to be executed when the endoscope 2 is repaired.

Furthermore, note that, though the mechanism configured to realize the function of illuminating and observing the lateral direction is included in the insertion portion 4 together with the mechanism configured to realize the function of illuminating and observing the forward direction in the second embodiment described above, the mechanism configured to realize the function of illuminating and observing the lateral direction may be a separate body attachable to and detachable from the insertion portion 4.

Figure 17:
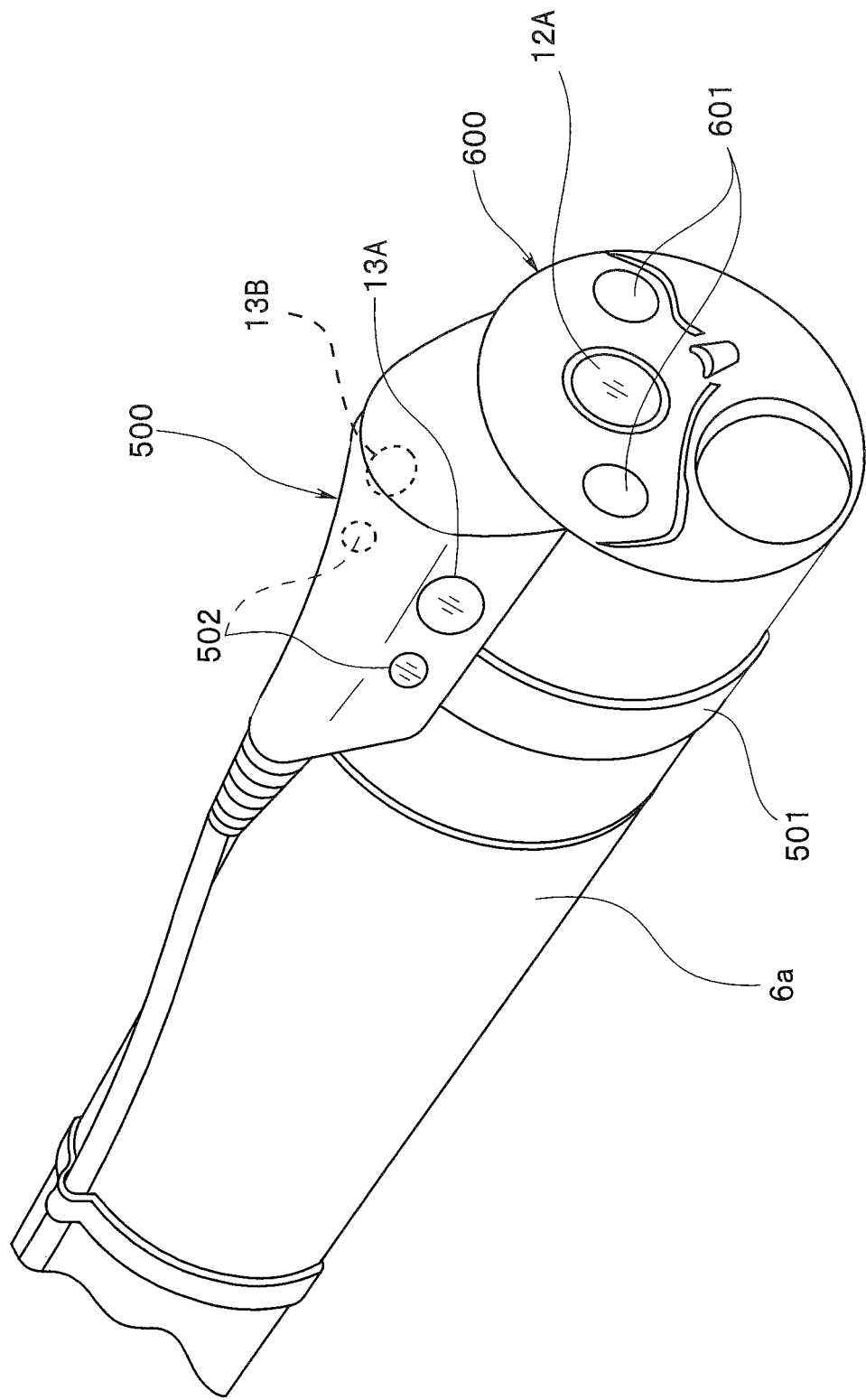
FIG. 17 is a perspective view of a distal end portion 6a of an insertion portion 4 to which a unit for lateral observation is fitted, according to a modification of the second embodiment of the present invention.

FIG. 17 is a perspective view of a distal end portion 6a of the insertion portion 4 to which a unit for lateral observation is fitted, according to a modification of the second embodiment. The distal end portion 6a of the insertion portion 4 has a forward-field-of-view unit 600. A lateral-field-of-view unit 500 has a configuration of being attachable to and detachable from the forward-field-of-view unit 600 by a clip portion 501.

The forward-field-of-view unit 600 has the forward observation window 12A for acquiring a forward-field-of-view image FV and an illuminating window 601 for illuminating the forward direction. The lateral-field-of-view unit 500 has the two lateral observation windows 13A and 13B for acquiring images in the left-and-right direction and two illuminating windows 502 for illuminating the left-and-right direction.

The video processor 32A and the like can perform acquisition and display of an observed image as shown in the embodiments described above by lighting up and lighting out each illuminating window 502 of the lateral-field-of-view unit 500 in accordance with a frame rate of a forward field of view.

As described above, according to the embodiment described above, it is possible to provide an endoscope system which, even if a displacement between optical systems for a forward-field-of-view image FV and a lateral-field-of-view image SV exists due to variation and the like in the processing accuracy of or at the time of assembly of the frame for fixing the lens of the objective optical system or the image pickup device, does not cause the user to feel unnatural from the forward-field-of-view image FV and the two lateral-field-of-view images SV1 and SV2 simultaneously displayed on the monitor 35, and an image processing method.

The present invention is not limited to the embodiments described above, and various changes, alterations and the like are possible within a range not changing the spirit of the present invention.

What is claimed is:

1. An endoscope system comprising:
   an insertion portion configured to be inserted into an inside of an object;
   a memory configured to store first information and second information;
   a first optical lens provided on the insertion portion and configured to acquire a first object image from a first area of the object, the first area including a forward direction of the insertion portion substantially parallel to a longitudinal direction of the insertion portion;
   a second optical lens provided on the insertion portion and configured to acquire a second object image from a second area of the object different from the first area, the second area including a lateral direction of the insertion portion substantially orthogonal to the longitudinal direction of the insertion portion;
   an image sensor configured to pick up the first object image and the second object image; and
   a processor comprising hardware, the processor being configured to:
   detect a positional relationship between a first image forming area where the first object image is formed and a second image forming area where the second object image is formed, on an image pickup surface of the image sensor;
   generate positional relationship detection information based on the positional relationship;
   store the positional relationship detection information as the first information into the memory;
   adjust a first reference point provided in the first image forming area and a second reference point provided in the second image forming area to correspond to each other based on the positional relationship detection information stored in the memory;
   cut out a central part image of the first object image from the first image forming area based on the positional relationship detection information stored in the memory;
   enlarge the central part image based on the second information stored in the memory;
   generate an image signal in which the enlarged central part image and the second object image are arranged with the first reference position provided in the first image forming area and the second reference position provided in the second image forming area; and
   perform a process for causing a position of at least one of the first object image and the second object image to change so that a displacement between coordinates of a center position of the first object image and coordinates of a center position of the second object image is corrected.

2. The endoscope system according to claim 1, wherein the positional relationship is shown by a first amount of displacement of the first image forming area relative to a predetermined position of an object image acquired by the image sensor and a second amount of displacement of the second image forming area relative to the predetermined position, and
   the positional relationship detection information includes the first amount of displacement and the second amount of displacement.

3. The endoscope system according to claim 1, wherein the first optical lens is arranged on a distal end portion in the longitudinal direction of the insertion portion, facing a direction in which the insertion portion is inserted; and
   the second optical lens is arranged on side face of the insertion portion, facing a radial direction of the insertion portion.

4. The endoscope system according to claim 1, wherein the image sensor is further configured to photoelectrically convert both of the first object image and the second object image on the image pickup surface.

5. The endoscope system according to claim 4, wherein the processor is further configured to receive the image signal and generate a display signal for displaying the image signal based on the first object image and the second object image on a display,
   wherein the first object image is displayed on the display so as to be in a substantially circular shape, and the second object image is displayed on the display so as to be in a substantially ring shape surrounding a circumference of the first object image.

6. The endoscope system according to claim 1, wherein the memory is further configured to store the positional relationship detection information,
   wherein the processor is further configured to generate an image signal in which arrangement of the first object image and the second object image is changed based on the positional relationship detection information stored in the memory until a positional relationship detection signal is updated.

7. The endoscope system according to claim 1, wherein the processor is further configured to generate an image signal in which the first object image and the second object image are arranged such that the at least one of the coordinates of the center position of the first object image and the coordinates of the center position of the second object image corresponds to a center of the image pickup surface which the image sensor picks up an image of.

8. The endoscope system of claim 1, wherein said second information comprises a predetermined radius of the first object image and a predetermined magnification value at which the first object image is magnified.

9. An endoscope video processor into which a first object image acquired from a first area of an object using an image sensor provided in an insertion portion of an endoscope inserted inside the object and a second object image acquired from a second area of the object using the image sensor are inputted, the first area including a forward direction of the insertion portion substantially parallel to a longitudinal direction of the insertion portion and the second area including a lateral direction of the insertion portion substantially orthogonal to the longitudinal direction of the insertion portion, the endoscope video processor configured to:
   detect a positional relationship between a first image forming area where the first object image is formed on an image pickup surface of the image sensor and a second image forming area where the second object image is formed on the image pickup surface;

generate positional relationship detection information based on the positional relationship;

store the positional relationship detection information into a memory;

adjust a first reference point provided in the first image forming area and a second reference point provided in the second image forming area to correspond to each other based on the positional relationship detection information;

cut out a central part image of the first object image from the first image forming area based on the positional relationship detection information;

enlarge the central part image based on other information read out from the memory;

generate an image signal in which the enlarged central part image and the second object image are arranged with the first reference position provided in the first image forming area and the second reference position provided in the second image forming area caused to correspond to each other based on the positional relationship detection information; and perform a process for causing a position of at least one of the first object image and the second object image to change so that a displacement between coordinates of a center position of the first object image and coordinates of a center position of the second object image is corrected.

10. The endoscope video processor of claim 9, wherein said other information comprises a predetermined radius of the first object image and a predetermined magnification value at which the first object image is magnified.

* * * * *